(12) United States Patent
Garvey et al.

(10) Patent No.: US 9,844,531 B2
(45) Date of Patent: Dec. 19, 2017

(54) METHODS OF MAINTAINING AND IMPROVING MUSCLE FUNCTION

(71) Applicant: ABBOTT LABORATORIES, Abbott Park, IL (US)

(72) Inventors: Sean Garvey, Columbus, OH (US); Suzette Pereira, Westerville, OH (US); Neile Edens, Austin, TX (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

(21) Appl. No.: 14/776,972

(22) PCT Filed: Mar. 14, 2014

(86) PCT No.: PCT/US2014/028879
§ 371 (c)(1),
(2) Date: Sep. 15, 2015

(87) PCT Pub. No.: WO2014/144458
PCT Pub. Date: Sep. 18, 2014

(65) Prior Publication Data
US 2016/0038457 A1    Feb. 11, 2016

Related U.S. Application Data

(60) Provisional application No. 61/792,489, filed on Mar. 15, 2013, provisional application No. 61/823,832, filed on May 15, 2013.

(51) Int. Cl.
| | | |
|---|---|---|
| A61K 31/353 | (2006.01) | |
| A23L 2/50 | (2006.01) | |
| A61K 9/00 | (2006.01) | |
| A23L 33/105 | (2016.01) | |

(52) U.S. Cl.
CPC .............. *A61K 31/353* (2013.01); *A23L 2/50* (2013.01); *A23L 33/105* (2016.08); *A61K 9/0053* (2013.01); *A23V 2002/00* (2013.01); *A23V 2200/316* (2013.01)

(58) Field of Classification Search
CPC ............................ A61K 31/35; A61K 31/353
USPC ......................................................... 514/456
See application file for complete search history.

(56) References Cited

U.S. PATENT DOCUMENTS

| | | | |
|---|---|---|---|
| 7,410,659 B2 | 8/2008 | Rosenbloom | |
| 7,572,599 B2 | 8/2009 | Lee et al. | |
| 7,678,363 B2 | 3/2010 | Barlow et al. | |
| 7,678,808 B2 | 3/2010 | Barlow et al. | |
| 7,858,611 B2 | 12/2010 | Barlow et al. | |
| 8,124,134 B2 | 2/2012 | Jia et al. | |
| 2007/0104807 A1* | 5/2007 | Gardiner ................. | A23L 1/293 424/729 |
| 2009/0163579 A1 | 6/2009 | Raederstorff et al. | |
| 2009/0281174 A1 | 11/2009 | Ota et al. | |
| 2010/0130597 A1* | 5/2010 | Chung ................... | A61K 45/06 514/44 R |
| 2010/0210692 A1 | 8/2010 | Farmer et al. | |
| 2010/0303937 A1 | 12/2010 | Farber | |
| 2011/0195932 A1 | 8/2011 | Wynne et al. | |

FOREIGN PATENT DOCUMENTS

| | | |
|---|---|---|
| EP | 1712140 B1 | 8/2008 |
| EP | 1961310 A1 | 8/2008 |
| EP | 2036551 A1 | 3/2009 |
| JP | 2006131512 A | 5/2006 |
| JP | 2009120491 A | 6/2009 |
| WO | 03053336 A2 | 7/2003 |
| WO | 2007042271 A2 | 4/2007 |
| WO | 2007126293 A1 | 11/2007 |
| WO | 2009064838 A1 | 5/2009 |
| WO | 2010118419 A2 | 10/2010 |
| WO | 2010143053 A1 | 12/2010 |
| WO | 2011011252 A1 | 1/2011 |
| WO | 2011089620 A2 | 7/2011 |
| WO | 2013142816 A1 | 9/2013 |
| WO | 2014028607 A1 | 2/2014 |
| WO | 2014055905 A1 | 4/2014 |

OTHER PUBLICATIONS

Malik et al., Expert Opin Emerg Drugs, Jun. 2012; 17(2): 261-277.*
International Search Report and Written Opinion for PCT/US2014/028879 dated Jul. 15, 2014.
International Preliminary Report on Patentability for PCT/US2014/028879 dated Sep. 15, 2015.
Communication Pursuant to Rules 161(1) and 162 for EP 14719586.1 dated Oct. 23, 2015.

(Continued)

*Primary Examiner* — Yong Chu
*Assistant Examiner* — Sonya Wright
(74) *Attorney, Agent, or Firm* — Porter Wright Morris & Arthur LLP

(57) ABSTRACT

Methods of decreasing muscle function decline and improving muscle function in a subject are provided. The methods utilize an effective amount of epigallocatechin-3-gallate (EGCg) to increase the level of muscle vascular endothelial growth factor A (VEGF), to decrease myostatin levels, or both, and thereby decrease muscle function decline or improve muscle function. The EGCg may be provided as part of a nutritional composition.

19 Claims, 4 Drawing Sheets

(56) References Cited

OTHER PUBLICATIONS

Office Action in Vietnam Patent Application No. 1-2015-03404 dated Feb. 2, 2016.
Arsic et al., "Vascular Endothelial Growth Factor Stimulates Skeletal Muscle Regeneration in Vivo," Molecular Therapy (2004), vol. 10, No. 5, 844-854.
Arthur et al., "The Effect of Physiological Stimuli on Sarcopenia; Impact of Notch and Wnt Signaling on Impaired Aged Skeletal Muscle Repair," Intl J Biol Sci (2012), vol. 8, No. 5, 731-760.
Buetler et al., "Green tea extract decreases muscle necrosis in mdx mice and protects against reactive oxygen species," Am J Clin Nutr (2002) vol. 75, 749-753.
Elkina et al., "The role of myostatin in muscle wasting: an overview," J Cachexia Sarcopenia Muscle (2011), vol. 2, 143-151.
Hüttemann et al., "(-)-Epicatechin is Associated with Increased Angiogenic and Mitochondrial Signaling in the Hindlimb of Rats Selectively Bred for Innate Low Running Capacity," Clin Sci (Lond) (2013), vol. 124, No. 11, 663-674.
Meng et al., "Effects of Epigallocatechin Gallate on Diethyldithiocarbamate-InducedPancreatic Fibrosis in Rats," Biol. Pharm. Bull. (2007), vol. 30, No. 6, 1091-1096.
Park et al., "Involvement of ERK and protein tyrosine phosphatase signaling pathways in EGCG-induced cyclooxygenase-2 expression in Raw 264.7 cells," Biochem. and Biophys. Res. Comm. (2001) vol. 286, 721-725, Abstract Only.
Pi et al., "EGCG regulates TGF-$\beta$1-induced epithelial mesenchymal transition insquamous cell carcinoma of head and neck," Zhonghua Er Bi Yan Hou Tou Jing Wai Ke Za Zhi. (Sep. 2012), vol. 47, No. 9, 749-752, Abstract Only.
Singh et al., Biochemical Pharmacology (2011), vol. 82, 1807-1821.
Testosterone Nation, Supplements and Nutrition Forum, "Wow! EGCG and Myostatin," http://tnation.t-nation.com/free_online_forum/diet_performance_nutrition_supplements/wow_4, Jun. 4, 2007.
Vittal et al., "Gene expression changes induced by green tea polyphenol (-)-epigallocatechin-3-gallate in human bronchial epithelial 21BES cells analyzed by DNA microarray," Mol Cancer Ther (2004), vol. 3, No. 9, 1091-1099.
Wagner, Kathryn R. "Muscle regeneration through myostatin inhibition," Curr Opin Rheumatol (2005), vol. 17, 720-724.
Zhu et al., "Myostatin signaling through Smad2, Smad3 and Smad4 is regulated bythe inhibitory Smad7 by a negative feedback mechanism," Cytokine (2004), vol. 26, No. 6, 262-272, Abstract Only.

* cited by examiner

METHODS OF MAINTAINING AND IMPROVING MUSCLE FUNCTION

CROSS REFERENCE TO RELATED APPLICATIONS

This application is the U.S. national stage entry of International Application No. PCT/US2014/028879, filed Mar. 14, 2014, which claims priority to and the benefit of U.S. Application No. 61/792,489, filed on Mar. 15, 2013, and U.S. Application No. 61/823,832, filed on May 15, 2013, the entire contents of which are incorporated herein by reference.

FIELD

The present disclosure relates to methods of decreasing muscle function decline in a subject in need thereof and methods of improving muscle function in a subject in need thereof. More particularly, the present disclosure relates to the use of an effective amount of epigallocatechin-3-gallate (EGCg) to decrease muscle function decline, to improve muscle function, or both in a subject in need thereof.

BACKGROUND

A certain level of muscle function is necessary for mobility and carrying out activities of daily living. A decline in muscle function can have a number of adverse effects on an individual including, but not limited to, general weakness, fatigue, a lessening of joint mobility, a reduction in physical activities, vulnerability to falls, and a general decline in functional status. A decline in muscle function may occur from a number of factors and conditions including, but not limited to, aging, sarcopenia, cachexia, immobilization as a result of bed rest, injury or slip-induced falls, diabetes, inflammation, ischemia reperfusion injury, intermittent claudication, peripheral arterial disease, chronic pulmonary obstructive disease, depression, and cognitive decline.

SUMMARY

Provided herein are methods of decreasing muscle function decline in a subject in need thereof and methods of improving muscle function in a subject in need thereof. The methods include administering epigallocatechin-3-gallate (EGCg) (or a source of EGCg) to a subject in need thereof in an amount effective to achieve at least one of the following: (1) an increase in the level of muscle VEGF; (2) an increase in muscle vasculature; (3) an increase in muscle blood flow; (4) a decrease in myostatin levels; and (5) inhibition of myostatin activity. In certain embodiments, the methods include administering EGCg as part of a nutritional composition.

In one exemplary embodiment, a method of decreasing muscle function decline in a subject in need thereof is provided. The method comprises administering epigallocatechin-3-gallate (EGCg) to a subject in need thereof in an amount effective to increase at least one of the level of muscle VEGF, muscle vasculature, or muscle blood flow, and thereby decrease muscle function decline in the subject in need thereof.

In one exemplary embodiment, a method of decreasing muscle function decline in a subject in need thereof is provided. The method comprises administering epigallocatechin-3-gallate (EGCg) to a subject in need thereof in an amount effective to decrease myostatin levels in the subject in need thereof, and thereby decrease muscle function decline in the subject in need thereof.

In one exemplary embodiment, a method of improving muscle function in a subject in need thereof is provided. The method comprises administering epigallocatechin-3-gallate (EGCg) to a subject in need thereof in an amount effective to increase at least one of the level of muscle VEGF, muscle vasculature, or muscle blood flow, and thereby improve muscle function in the subject in need thereof.

In one exemplary embodiment, a method of improving muscle function in a subject in need thereof is provided. The method comprises administering epigallocatechin-3-gallate (EGCg) to a subject in need thereof in an amount effective to decrease myostatin levels in the subject in need thereof, and thereby improve muscle function in the subject in need thereof.

In one exemplary embodiment, a nutritional composition for decreasing muscle function decline, improving muscle function, or both in a subject in need thereof is provided. The nutritional composition comprises at least one source of protein in an amount sufficient to provide 6 grams to 50 grams of protein per serving, and 0.1 grams to 3 grams of epigallocatechin-3-gallate (EGCg) per serving. Consumption of the nutritional composition by the subject in need thereof results in at least one of the following: (1) an increase in the level of muscle VEGF; (2) an increase in muscle vasculature; (3) an increase in muscle blood flow; (4) a decrease in myostatin levels; and (5) inhibition of myostatin activity. Accordingly, consumption of the nutritional composition can decrease muscle function decline, improve muscle function, or both in the subject in need thereof.

DETAILED DESCRIPTION

Figure 1A:
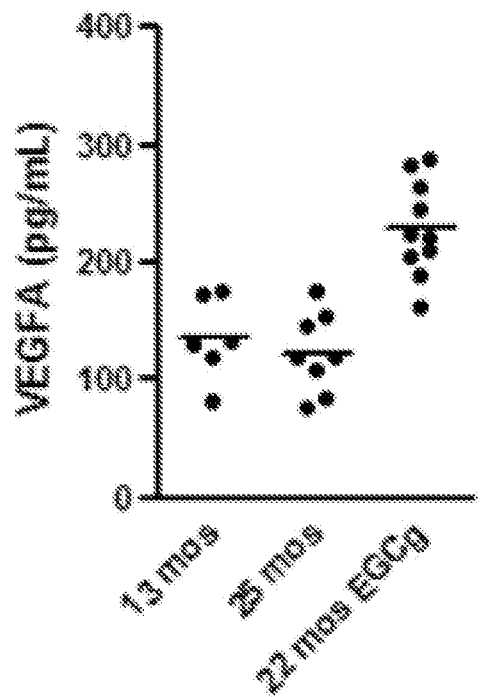
FIGS. 1A and 1B show that 8 weeks of dietary EGCg supplementation causes a significant increase in the level of VEGF and a significant decrease in the level of interleukin-1A (IL1A) in aged Sprague Dawley (SD) rat gastrocnemius muscle.

Methods of decreasing muscle function decline in a subject in need thereof and methods of improving muscle function in a subject in need thereof are provided. The methods include administering epigallocatechin-3-gallate (EGCg) to a subject in need thereof in an amount effective to achieve at least one of the following: (1) an increase in the level of muscle VEGF; (2) an increase in muscle vasculature; (3) an increase in muscle blood flow; (4) a decrease in myostatin levels; and (5) inhibition of myostatin activity. In certain embodiments, the methods include administering EGCg as part of a nutritional composition.

The terminology as set forth herein is for description of the embodiments only and should not be construed as limiting the disclosure as a whole. Unless otherwise specified, "a," "an," "the," and "at least one" are used interchangeably. Furthermore, as used in the description and the appended claims, the singular forms "a," "an," and "the" are inclusive of their plural forms, unless the context clearly indicates otherwise.

The term "nutritional composition" as used herein, unless otherwise specified, refers to nutritional products in various forms including, but not limited to, liquids, solids, powders, semi-solids, semi-liquids, nutritional supplements, and any other nutritional food product known in the art. A nutritional composition in powder form may often be reconstituted to form a nutritional composition in liquid form. In certain embodiments, the nutritional composition comprises at least one source of protein in an amount sufficient to provide 6 grams to 50 grams of protein per serving. In certain other embodiments, the nutritional composition further comprises at least one source of carbohydrate, at least one source of fat, or both. The nutritional compositions disclosed herein are generally suitable for oral consumption by a human.

The term "subject" as used herein, unless otherwise specified, refers to a mammal, including companion animals, livestock, laboratory animals, working animals, sport animals, and humans. In certain embodiments, the subject is a human.

The term "subject in need thereof" as used herein, unless otherwise specified, refers to a subject exhibiting muscle loss due at least in part to age, inactivity, injury, disease, or combinations thereof. In certain embodiments, the muscle loss in the subject in need thereof is at least partially attributable to increased muscle protein degradation, decreased muscle protein synthesis, decreased muscle regeneration, or combinations thereof. In certain embodiments, the subject in need thereof, is an elderly human, optionally an inactive elderly human, optionally a diseased elderly human, and optionally both inactive and diseased. In certain embodiments, the subject in need thereof is a human that is undergoing a temporary or permanent period of inactivity, due to disability, temporary injury, or healing from an operation. In certain embodiments, the subject in need thereof is a human undergoing rehabilitation (i.e., physical rehabilitation) due to disease, injury, surgery, hospital admission, and combinations thereof. In certain embodiments, the subject in need thereof has reduced intramuscular blood flow due to attenuation of endothelin-dependent muscle blood flow or other mechanisms. In certain embodiments, the subject in need thereof is a human with a chronic disease condition such as, for example, cancer cachexia, chronic obstructive pulmonary disease (COPD), or end-stage renal disease. In certain embodiments, the subject in need thereof is a human undergoing treatment with glucocorticoids for an extended period of time. In certain embodiments, the subject in need thereof is a human suffering from a muscle disease such as, for example, muscular dystrophy.

The term "elderly" as used herein, refers to an individual of at least 45 years of age, including at least 50 years of age, at least 55 years of age, at least 60 years of age, at least 65 years of age, at least 70 years of age, at least 75 years of age, and including at least 80 years of age or greater. The term "elderly" also includes the groups of from 45 years of age to 100 years of age, and the group of from 55 years of age to 80 years of age.

The terms "administer," "administering," "administered," and "administration" as used herein, unless otherwise specified, should be understood to include providing an active ingredient (or nutritional product containing the active ingredient) to a subject, the act of consuming the active ingredient, and combinations thereof. In addition, it should be understood that the methods disclosed herein (e.g., administering) may be practiced with or without doctor supervision or other medical direction.

The term "effective amount" as used herein, unless otherwise specified, refers to a sufficient amount of an active ingredient (e.g., EGCg) to achieve at least one of the following: (1) an increase in the level of muscle VEGF; (2) an increase in muscle vasculature; (3) an increase in muscle blood flow; (4) a decrease in myostatin levels; and (5) inhibition of myostatin activity; and to exhibit a therapeutic effect (e.g., maintain muscle function, improve muscle function, attenuate muscle function decline). The exact amount required will vary from subject to subject, depending on the species, age, weight, lifestyle and general condition of the particular subject.

The term "nutritional liquid" as used herein, unless otherwise specified, refers to nutritional compositions in ready-to-drink liquid form, concentrated liquid form, and nutritional liquids made by reconstituting nutritional powders described herein prior to use. The nutritional liquid may also be formulated as a suspension, an emulsion, a solution, and so forth.

The terms "nutritional powder" and "reconstitutable powder" as used herein, unless otherwise specified, refer to nutritional compositions in flowable or scoopable form that can be reconstituted with water or another aqueous liquid prior to consumption and includes both spray dried and drymixed/dryblended powders.

The term "nutritional semi-solid" as used herein, unless otherwise specified, refers to nutritional products that are intermediate in properties, such as rigidity, between solids and liquids. Some semi-solid examples include puddings, yogurts, gels, gelatins, and doughs.

The term "nutritional semi-liquid" as used herein, unless otherwise specified, refers to nutritional compositions that are intermediate in properties, such as flow properties, between liquids and solids. Some semi-liquids examples include thick shakes, liquid yogurts, and liquid gels.

The term "serving" as used herein, unless otherwise specified, is intended to be construed as any amount which is intended to be consumed by a subject in one sitting or within one hour or less.

The term "muscle" as used herein, unless otherwise specified, refers to skeletal muscle and other non-skeletal, striated muscles such as diaphragm, extraocular muscle, and so forth.

The term "intramuscular" as used herein, unless otherwise specified, refers to all cellular parts that comprise a skeletal muscle group including, but not limited to, myofibers, myoblasts, satellite cells, neurons, endothelial cells, pericytes, monocytes, macrophages, adipocytes, and fibroblasts.

The term "muscle mass" as used herein, unless otherwise specified, refers to the amount or size of muscle or muscle groups, as expressed by muscle weight, mass, area, or volume. Muscle mass may also be expressed as total lean body mass, lean body mass of a body compartment such as the leg, or cross-sectional area of a leg or arm compartment. The volume or mass of the muscle can be determined using any known or otherwise effective technique that provides muscle area, volume, or mass, such as DEXA, or using visual or imaging techniques such as MRI or CT scans.

The term "muscle atrophy" as used herein, unless otherwise specified, refers to the loss of muscle mass (also known as muscle wasting). Muscle atrophy may be caused by normal aging (e.g., sarcopenia), inactivity (e.g., muscle disuse or immobility), or disease-related disorders (e.g., cachexia).

The term "muscle strength" as used herein, unless otherwise specified, refers to the amount of force a muscle, or muscle groups in sum, can exert. Muscle strength may be evaluated by a variety of methods such as grip strength, one repetition maximum strength test, time-dependent tests of muscle endurance, time-dependent tests of muscle fatigue, or time-dependent tests of muscle endurance and fatigue, and so forth.

The term "muscle function" as used herein, unless otherwise specified, refers to at least one of muscle mass and muscle strength.

The term "providing" as used herein within the context of providing a nutritional composition or an amount of an active ingredient (e.g., EGCg) to a subject according to a certain regimen or schedule, should be understood to reflect a subject who has been instructed to be administered the active ingredient, and who actually is administered the nutritional composition or amount of active ingredient for at least 70% of the days during the desired period of the regimen or schedule. In other embodiments, providing a nutritional composition or an amount of an active ingredient (e.g., EGCg) to a subject according to a certain regimen or schedule, should be understood to reflect a subject who has been instructed to be administered the active ingredient, and who actually is administered the nutritional composition or amount of active ingredient for at least 90% of the days during the desired period of the regimen or schedule.

The term "VEGF" as used herein refers to vascular endothelial growth factor A (i.e., VEGF-A).

In one exemplary embodiment, a method of decreasing muscle function decline in a subject in need thereof is provided. The method comprises administering epigallocatechin-3-gallate (EGCg) to a subject in need thereof in an amount effective to increase at least one of the level of muscle VEGF, muscle vasculature, or muscle blood flow, and thereby decrease muscle function decline in the subject.

In one exemplary embodiment, a method of decreasing muscle function decline in a subject in need thereof is provided. The method comprises administering epigallocatechin-3-gallate (EGCg) to a subject in need thereof in an amount effective to decrease myostatin levels in the subject, and thereby decrease muscle function decline in the subject.

In one exemplary embodiment, a method of improving muscle function in a subject in need thereof is provided. The method comprises administering epigallocatechin-3-gallate (EGCg) to a subject in need thereof in an amount effective to increase at least one of the level of muscle VEGF, muscle vasculature, or muscle blood flow, and thereby improve muscle function in the subject.

In one exemplary embodiment, a method of improving muscle function in a subject in need thereof is provided. The method comprises administering epigallocatechin-3-gallate (EGCg) to a subject in need thereof in an amount effective to decrease myostatin levels in the subject, and thereby improve muscle function in the subject.

In one exemplary embodiment, a method of decreasing muscle function decline, improving muscle function, or both in a subject in need thereof is provided. The method comprises administering epigallocatechin-3-gallate (EGCg) to the subject in need thereof in an amount effective to: (a) increase at least one of: (i) the level of muscle VEGF; (ii) muscle vasculature; and (iii) muscle blood flow; (b) decrease myostatin levels in the subject in need thereof; and (c) combinations of (a) and (b); and thereby decreasing muscle function decline, improving muscle function, or both in the subject need thereof.

In one exemplary embodiment, a nutritional composition for decreasing muscle function decline, improving muscle function, or both in a subject in need thereof is provided. The nutritional composition comprises at least one source of protein in an amount sufficient to provide 6 grams to 50 grams of protein per serving, and 0.1 grams to 3 grams of epigallocatechin-3-gallate (EGCg) per serving. Consumption of the nutritional composition by the subject in need thereof results in at least one of the following: (1) an increase in the level of muscle VEGF; (2) an increase in muscle vasculature; (3) an increase in muscle blood flow; (4) a decrease in myostatin levels; and (5) inhibition of myostatin activity. Accordingly, consumption of the nutritional composition can decrease muscle function decline, improve muscle function, or both in the subject in need thereof.

According to certain exemplary embodiments, the methods described herein include the administration of an amount of EGCg effective to increase the level of muscle (i.e., intramuscular) VEGF in a subject in need thereof. VEGF is a circulating protein in the vasculature that mediates vascular permeability and induces angiogenesis. In addition, VEGF assists in controlling basal muscle capillarization and regulating exercise-induced angiogenesis. Moreover, increased expression of VEGF and VEGF pathway genes in muscle cells contributes to myogenic differentiation. Therefore, an increase in the level of muscle VEGF can increase muscle vasculature, muscle blood flow, and muscle oxygenation via angiogenesis, and thereby decrease muscle function decline, improve muscle function, or both. In addition, an increase in the level of muscle VEGF improves muscle healing by promoting uptake of circulating reparatory cells, and also improves muscle growth, and thereby decrease muscle function decline, improve muscle function, or both.

The methods according to certain exemplary embodiments include the administration of an amount of EGCg effective to decrease myostatin levels in a subject in need thereof. Myostatin (also known as growth differentiation factor-8, GDF-8) is a secreted cytokine, expressed predominantly in skeletal muscle, that regulates muscle regeneration and hypertrophy, as well as opposes the action of certain growth factors. Specifically, myostatin negatively regulates muscle mass, hypertrophy, and regeneration, in part, to prevent aberrant growth of muscle tissue. For example, myostatin binds to the activin receptors at the plasma cell membrane and initiates a series of downstream signaling cascades that: 1) activate MAPK signaling, resulting in an inhibition of the myogenesis-promoting gene expression program (e.g., myoD and myogenin); and 2) inhibit Akt phosphorylation, resulting in activation of FoxO dependent protein degradation and inhibition of cyclin D1, a cell division regulator.

It has been hypothesized that myostatin negatively regulates muscle regeneration and growth with advancing age. In one particular study, serum myostatin was found to be increased in older (60-92 year-old) women and men, compared to younger (19-35 year-old) women and men. (Yarasheski et al., *J. Nutr. Health Aging*, 6, 343-348 (2002)). In the same study, serum myostatin was also negatively correlated with fat-free mass and muscle mass in the elderly subjects.

Moreover, the effect of myostatin on muscle regeneration has been demonstrated in murine models. For example, myostatin deficiency was shown to result in a more pronounced regenerative muscle response following acute injury with cardiotoxin. (Wagner et al., *Proc. Natl. Acad. Sci. U.S.A*, 102, 2519-2524 (2005)). In this same study, muscle progenitor cells from myostatin knockout mice were shown to proliferate at a higher rate than those from littermate controls. Additional studies have shown that inhibition of myostatin enhances muscle progenitor cell activation and proliferation, or that administration of myostatin inhibits muscle progenitor cell activation and proliferation. (Joulia et al., *Exp. Cell Res.*, 286, 263-275 (2003)). Furthermore, myostatin deficiency prevented muscle atrophy and blocked glucocorticoid-induced expression of proteolytic enzymes following dexamethasone treatment in mice. (Gilson et al., *Endocrinology*, 148, 452-460 (2007)).

Accordingly, inhibiting or decreasing myostatin expression in the muscle promotes muscle regeneration and muscle hypertrophy. Improved muscle regeneration and hypertrophy can lead to increases in muscle mass and muscle strength, and thereby decrease muscle function decline, improve muscle function, or both.

EGCg is a polyphenol, more specifically a flavan-3-ol or catechin, that exhibits anti-oxidant and anti-inflammatory properties. As used herein, the term "EGCg" refers to epigallocatechin-3-gallate, or a source thereof. Generally, EGCg is the most abundant polyphenol present in green tea. A number of studies have investigated therapeutic uses of green tea catechins, and EGCg in particular, and have found that EGCg and green tea catechins exhibit anti-angiogenic (and thus anti-tumorigenic) activity and inhibit VEGF production. Accordingly, the increase in the level of muscle VEGF effected by the administration of EGCg in accordance with the presently disclosed methods was an unexpected and surprising result. In addition, the inventors have discovered that administration of an effective amount of EGCg (or a source thereof) decreases myostatin levels, which in turn decreases muscle function decline, improves muscle function, or both.

In accordance with the methods disclosed herein, the EGCg can be formulated in a suitable composition (e.g., a nutritional composition) and then, in accordance with the methods described herein, administered to a subject in a form adapted to the chosen route of administration. The compositions according to the methods disclosed herein include those suitable for oral administration. Oral administration, as defined herein, includes any form of administration in which the EGCg passes through the esophagus of the subject. For example, oral administration includes nasogastric intubation, in which a tube is run from through the nose to the stomach of the subject to administer food or drugs.

Pharmaceutical and nutritional compositions containing EGCg can also be referred to herein as medicaments. For example, EGCg can be used for the preparation of a medicament for treating a subject in need of muscle function improvement.

In certain exemplary embodiments, the EGCg is administered to the subject orally. Generally, an effective amount of EGCg may be provided in any form suitable for oral consumption by the subject. For example, the EGCg may be provided as caplets, tablets, pills, capsules, chewable tablets, quick dissolve tablets, effervescent tablets, solutions, suspensions, emulsions, multi-layer tablets, bi-layer tablets, soft gelatin capsules, hard gelatin capsules, lozenges, chewable lozenges, beads, granules, particles, microparticles, dispersible granules, cachets, and combinations thereof. According to certain exemplary embodiments, the EGCg is provided as part of a nutritional composition, which will be discussed in more detail below.

The EGCg used in connection with the methods disclosed herein may be provided by natural or synthetic sources. Suitable sources of EGCg for use in the methods disclosed herein are green tea-based sources including, but not limited to, green tea extracts in which EGCg alone, or in combination with other polyphenol compounds (e.g., flavan-3-ols), are isolated from green tea as an extract. Examples of such suitable green tea extracts are in the form of a liquid with a high concentration of the polyphenols, a solid (e.g., a powder), and mixtures thereof. In certain embodiments where a green tea extract is utilized, the extract is decaffeinated such that it contains less than 1% by weight caffeine, or even less than 0.5% by weight caffeine. In addition to containing EGCg, suitable green tea extracts used in connection with the methods disclosed herein may contain other polyphenols including other flavan-3-ols such as catechin (e.g., (+)-catechin, also known as "C"), epicatechin ("EC"), gallocatechin ("GC"), epigallocatechin ("EGC"), and epicatechin gallate ("ECg"), and stereoisomers thereof flavones such as apigenin, isoviloxin, sapotarin, and vicenin-2; flavonols such as kaempherol, quercetin, and myricetin; condensed flavanoids; and tannin glycosides. Accordingly, in certain exemplary embodiments, in addition to EGCg, the subject is administered one or more flavan-3-ols selected from the group consisting of C, EC, GC, EGC, and ECg. In addition, in certain exemplary embodiments, the EGCg, C, EC, GC, EGC, and ECg are administered as part of a nutritional composition.

In certain exemplary embodiments, sources of EGCg other than green tea-based sources may be utilized. These sources include, but are not limited to, oolong tea-based sources such as oolong tea, oolong tea extracts, and the like; white tea-based sources such as white tea, white tea extracts, and the like; macha tea, macha tea extracts, and the like; yellow tea, yellow tea extracts, and the like; and dark tea (i.e., Chinese dark tea), dark tea extracts, and the like.

In certain exemplary embodiments, the EGCg is provided at least in part by a green tea extract. In certain exemplary embodiments, when the EGCg is provided as part of a green tea extract, the green tea extract contains at least 20% by weight EGCg. In other embodiments, when the EGCg is provided as part of a green tea extract, the green tea extract contains at least 45% by weight EGCg. In certain exemplary embodiments, the EGCg is provided at least in part by a green tea extract that contains 20-100% by weight EGCg. In certain exemplary embodiments, the EGCg is provided as part of a green tea extract that contains 45-100% by weight EGCg, including 50-100% by weight EGCg, including 60-100% by weight EGCg, including 70-100% by weight EGCg, including 80-100% by weight EGCg, and also including 90-100% by weight EGCg. Examples of commercially available sources of EGCg provided as part of a green tea extract include Teavigo® (>90% EGCg) (DSM, Netherlands) and Sunphenon® 90D (Taiyo International, Inc., Minneapolis, Minn.).

In accordance with the methods disclosed herein, compositions including an effective amount of EGCg, such as a green tea extract or a nutritional composition containing EGCg, can be provided to a subject in need thereof in one or multiple doses, or servings, over a period of time. In certain embodiments according to the methods disclosed herein, an effective amount of EGCg is provided or administered to a subject in need thereof in two doses or servings per day. In other embodiments according to the methods disclosed herein, an effective amount of EGCg (or a source thereof) is provided or administered to a subject in need thereof in multiple (e.g., two, three, four, or more) servings per day. In certain other embodiments, an effective amount of EGCg (or a source thereof) is provided or administered to a subject in need thereof within 2 hours of waking, within 2 hours of sleeping, or both within 2 hours of waking and within 2 hours of sleeping.

In accordance with the methods disclosed herein, the effective amount of EGCg (or a source thereof) can be administered to (or consumed by) a subject in need thereof one or more times per day for a period suitable to achieve the desired effect. For example, a composition comprising an effective amount of EGCg can be administered to a subject in need thereof every day for at least a week, every day for at least two weeks, every day for at least a month, every day for at least 6 months, or every day for a year or more. As another example, a composition comprising an effective amount of EGCg can be administered to a subject in need thereof twice a day for at least a week, twice a day for at least two weeks, twice a day for at least a month, twice a day for at least 6 months, or twice a day for a year or more. Within the context of providing a dose to a subject, every day is intended to reflect a subject who has been instructed to be administered the EGCg (or a source of EGCg) every day, and who actually is administered the EGCg for at least 70%, and in certain embodiments at least 90%, of the days during the desired period of administration.

In some embodiments, the effective amount of EGCg (or a source thereof, or composition containing either EGCg or a source thereof) is chronically administered. "Chronically administering" refers, in one embodiment, to regular administration which is provided indefinitely. In other embodiments, the term refers to regular administration for a significant period of time. For example, in different embodiments chronic administration can include regular administration for at least one month, regular administration for at least 6 weeks, regular administration for at least two months, regular administration for at least 3 months, regular administration for at least 4 months, regular administration for at least 5 months, regular administration for at least 6 months, or regular administration for at least 9 months. In further embodiments, the chronic administration refers to regular administration for at least 1 year, regular administration for at least 1.5 years, regular administration for at least 2 years, or regular administration for more than 2 years. "Regular administration" refers to administration according to a schedule where it is intended that the subject in need thereof will receive the EGCg (or a source of EGCg) at regular intervals.

As used herein, "regular intervals" refers to administration in a repeating, periodic fashion where the time between administrations is approximately (or intended to be approximately) the same. In various embodiments, administration at regular intervals includes daily administration or weekly administration. In further embodiments, the term refers to administration 1-2 times per week, administration 1-3 times per week, administration 2-3 times per week, administration 1-4 times per week, administration 1-5 times per week, administration 2-5 times per week, administration 3-5 times per week, administration 1-6 times per week, administration 1-7 times per week, administration 2-6 time per week, administration 2-7 times per week, administration 1-2 times per day, administration 1-3 times per day, administration 1-4 times per day, administration 2-3 times per day, administration 2-4 times per day, administration 3-4 times per day, administration 2-5 times per day, administration 3-5 times per day, or administration 4-5 times per day.

In certain exemplary embodiments, the total amount of EGCg administered ranges from 0.1 g/day to 3 g/day, including from 0.5 g/day to 2.5 g/day, and also including from 1 g/day to 2 g/day. In certain exemplary embodiments, the total amount of EGCg administered ranges from 0.05 g/serving to 1.5 g/serving, including from 0.1 g/serving to 1.25 g/serving, and also including from 0.5 g/serving to 1 g/serving. In certain embodiments, the total amount of EGCg is provided in two servings per day. In certain embodiments, an effective amount of EGCg corresponds to the total amount of EGCg administered to a subject in need thereof (e.g., from 0.1 g/day to 3 g/day and other amounts previously mentioned). As previously mentioned, an effective amount of EGCg refers to a sufficient amount of EGCg to achieve at least one of the following: (1) an increase in the level of muscle VEGF; (2) an increase in muscle vasculature; (3) an increase in muscle blood flow; (4) a decrease in myostatin levels; and (5) inhibition of myostatin activity; and to exhibit a therapeutic effect (e.g., maintain muscle function, improve muscle function, attenuate muscle function decline). In addition, the exact amount of EGCg required to achieve the desired effects will vary depending on the particular subject.

As mentioned above, according to certain exemplary embodiments, the EGCg is provided as part of a nutritional composition. In certain embodiments, the nutritional compositions are formulated as, and intended for consumption in, any known or otherwise suitable oral product form. Any solid, liquid, semi-solid, semi-liquid, or powder product form, including combinations or variations thereof, are suitable for use herein, provided that such forms allow for safe and effective oral delivery to the subject via oral consumption of the ingredients as also defined herein.

In certain exemplary embodiments, the nutritional composition is a solid nutritional product. Non-limiting examples of solid nutritional products include snack and meal replacement products, including those formulated as bars, sticks, cookies or breads or cakes or other baked goods, frozen liquids, candy, breakfast cereals, powders or granulated solids or other particulates, snack chips or bites, frozen or retorted entrees and so forth. In certain exemplary embodiments, when the nutritional composition is a solid product, the serving is within a range of 25 grams to 150 grams.

In certain exemplary embodiments, the nutritional composition is a nutritional liquid. Non-limiting examples of nutritional liquids include snack and meal replacement products, hot or cold beverages, carbonated or non-carbonated beverages, juices or other acidified beverages, milk or soy-based beverages, shakes, coffees, teas, compositions for administration by nasogastric intubation, and so forth. Generally, the nutritional liquids are formulated as suspensions or emulsions, but the nutritional liquids can also be formulated in any other suitable forms such as clear liquids, solutions, liquid gels, liquid yogurts, and so forth.

In certain embodiments where the nutritional composition is a liquid, the serving is within a range of 30 milliliters to 500 milliliters (~1 fl. oz. to ~17 fl. oz.). In certain embodiments where the nutritional composition is a liquid, the serving is 237 milliliters (~8 fl. oz.). In certain embodiments where the nutritional composition is a liquid, the serving is 125 milliliters (~4 fl. oz.). In other embodiments where the nutritional composition is a liquid, the serving is 177 milliliters to 417 milliliters (~6 fl. oz. to ~14 fl. oz.). In yet other embodiments where the nutritional composition is a liquid, the serving is 207 milliliters to 266 milliliters (~7 fl. oz. to ~9 fl. oz.). In still other embodiments where the nutritional composition is a liquid, the serving is 30 milliliters to 75 milliliters (~1 fl. oz. to ~2.5 fl. oz.). In certain embodiments where the nutritional composition is administered as a liquid, one serving to 14 servings of the nutritional composition is administered to the subject per week.

In certain exemplary embodiments, the nutritional composition may be formulated as semi-solid or semi-liquid compositions (e.g., puddings, gels, yogurts, etc.), as well as more conventional product forms such as capsules, tablets, caplets, pills, and so forth. In other embodiments, the nutritional composition may be in the form of lozenges, tablets (e.g., chewable, coated), pastes, gels, or yogurts.

The nutritional compositions disclosed herein are useful to provide sole, primary, or supplemental sources of nutrition, as well as providing one or more of the benefits as described herein. Accordingly, the nutritional compositions disclosed herein may include one or more macronutrients. For example, in certain exemplary embodiments, the nutritional composition comprises at least one source of fat, at least one source of carbohydrates, and at least one source of protein. In certain exemplary embodiments, the nutritional composition comprises at least one source of protein, at least one source of carbohydrates, but no source of fat (although the nutritional composition may comprise a trace amount of fat inherent from, for example, the protein source). In certain exemplary embodiments, the nutritional composition provides up to 1000 kcal of energy per serving or dose, including from 20 kcal to 900 kcal, from 25 kcal to 700 kcal, from 50 kcal to 500 kcal, from 100 kcal to 450 kcal, or from 150 kcal to 400 kcal per serving.

In accordance with certain exemplary embodiments, the nutritional composition comprises at least one source of protein in an amount sufficient to provide 6 grams to 50 grams of protein per serving of the nutritional composition. In certain exemplary embodiments, the nutritional composition comprises 6 grams to 50 grams of protein per serving, including 9 grams to 40 grams of protein, including 9 grams to 35 grams of protein, and also including 9 grams to 30 grams of protein per serving. In certain other exemplary embodiments, the at least one source of protein comprises 1% to 40% of the nutritional composition, by weight, including from 5% to 30%, including from 10% to 25%, including from 15% to 20%, and also including from 1% to 5% by weight of the composition. A wide variety of protein sources may be used so long as it is suitable for use in oral nutritional compositions and is otherwise compatible with any other selected ingredients or features in the nutritional composition. In certain exemplary embodiments, the at least one source of protein may include a mixture of amino acids (often described as free amino acids) known for use in nutritional products, including the amino acids described herein, or a combination of such amino acids with the intact, hydrolyzed, and partially hydrolyzed proteins described herein. The amino acids may be naturally occurring or synthetic amino acids, or combinations thereof.

The source of protein may include, but is not limited to, intact, hydrolyzed, and partially hydrolyzed protein, which may be derived from any known or otherwise suitable source such as milk (e.g., casein, whey), animal (e.g., meat, fish), cereal (e.g., rice, corn), vegetable (e.g., soy, pea), insect (e.g., cricket, locust), and combinations thereof. Non-limiting examples of the source of protein include whey protein concentrates, whey protein isolates, whey protein hydrolysates, acid caseins, sodium caseinates, calcium caseinates, potassium caseinates, casein hydrolysates, milk protein concentrates, milk protein isolates, milk protein hydrolysates, nonfat dry milk, condensed skim milk, soy protein concentrates, soy protein isolates, soy protein hydrolysates, pea protein concentrates, pea protein isolates, pea protein hydrolysates, collagen proteins, collagen protein concentrates, collagen protein isolates, insect protein, earthworm protein, and combinations thereof. In addition, the at least one source of protein in an amount sufficient to provide 6 grams to 50 grams of protein per serving may comprise any one source of protein or any combination of the various sources of protein provided in the non-limiting list presented above.

In certain exemplary embodiments when the nutritional composition is formulated as a clear liquid nutritional product having a pH ranging from 2 to 5, the source of protein suitable for use in the clear liquid nutritional product is selected from the group consisting of whey protein isolate, whey protein concentrates, whey protein hydrolysates, casein hydrolysates, soy protein hydrolysates, pea protein hydrolysates, collagen proteins, collagen protein isolates, soy protein isolates, insect protein isolates, and combinations thereof. These particular sources of protein are suitable for use in a clear liquid nutritional product as they are soluble at lower pH ranges, which allows the liquid nutritional product to provide a desired amount of protein, yet remain clear. In addition, in certain embodiments, the source of protein suitable for use in the clear liquid nutritional product may provide 6 grams to 50 grams of protein per serving, and may comprise any one source of protein or any combination of the various sources of protein provided in the non-limiting list of suitable proteins for use in the clear liquid nutritional product.

In addition to the at least one source of protein, in certain exemplary embodiments the nutritional composition further comprises at least one source of carbohydrates, or at least one source of fat, or combinations thereof. Therefore, in certain embodiments the nutritional composition further comprises at least one source of carbohydrates, while in other embodiments the nutritional composition further comprises at least one source of fat, and yet in other embodiments the nutritional composition further comprises at least one source of carbohydrates and at least one source of fat.

In certain exemplary embodiments, the nutritional composition further comprises at least one source of carbohydrates. In some exemplary embodiments where the nutritional composition contains at least one source of carbohydrates, the at least one source of carbohydrates comprises from 10% to 80% by weight of the nutritional composition, including from 30% to 60%, and also including from 50% to 70% by weight of the nutritional composition. In other exemplary embodiments, the nutritional composition comprises 15 grams to 110 grams of at least one source of carbohydrates per serving. In other exemplary embodiments, the nutritional composition comprises 25 grams to 90 grams of at least one source of carbohydrates per serving, including 40 grams to 65 grams of at least one source of carbohydrates per serving, and also including 45 grams to 55 grams of at least one source of carbohydrates per serving.

The at least one source of carbohydrates suitable for use in certain embodiments of the nutritional compositions disclosed herein may be simple, complex, or variations or combinations thereof. Generally, any source of carbohydrates may be used so long as it is suitable for use in oral nutritional compositions and is otherwise compatible with any other selected ingredients or features present in the nutritional composition. Non-limiting examples of a source of carbohydrates suitable for use in the nutritional compositions described herein include maltodextrin, hydrolyzed or modified starch or cornstarch, glucose polymers, corn syrup, corn syrup solids, rice-derived carbohydrates, sucrose, glucose, fructose, lactose, high fructose corn syrup, honey, sugar alcohols (e.g., maltitol, erythritol, sorbitol), isomaltulose, sucromalt, pullulan, potato starch, and other slowly-digested carbohydrates, dietary fibers including, but not limited to, fructooligosaccharides (FOS), galactooligosaccharides (GOS), oat fiber, soy fiber, gum arabic, sodium carboxymethylcellulose, methylcellulose, guar gum, gellan gum, locust bean gum, konjac flour, hydroxypropyl methylcellulose, tragacanth gum, karaya gum, gum acacia, chitosan, arabinoglactins, glucomannan, xanthan gum, alginate, pectin, low and high methoxy pectin, cereal beta-glucans (e.g., oat beta-glucan, barley beta-glucan), carrageenan, psyllium, digestion resistant maltodextrin (e.g., Fibersol®-2 available from ADM/Matsutani, LLC (Iowa, USA)), other resistant starches, and combinations thereof.

In certain exemplary embodiments, the nutritional composition further comprises at least one source of fat. In other exemplary embodiments, the nutritional composition comprises no fat, or essentially no fat (i.e., less than 0.5 grams of fat per serving). In certain exemplary embodiments where the nutritional composition contains fat, the nutritional composition comprises from 0.5 grams to 45 grams of at least one source of fat per serving. In other exemplary embodiments, the nutritional composition comprises from 5 grams to 35 grams of at least one source of fat per serving, including from 10 grams to 30 grams of at least one source of fat per serving, and also including from 15 grams to 25 grams of at least one source of fat per serving. In certain exemplary embodiments where the nutritional composition comprises at least one source of fat, the at least one source of fat comprises from 1% to 30% by weight of the nutritional composition, including from 5% to 25% by weight of the nutritional composition, including from 10% to 20% by weight of the nutritional composition, and also including from 12% to 18% by weight of the nutritional composition.

In general, any source of fat may be used so long as it is suitable for use in oral nutritional compositions and is otherwise compatible with any other selected ingredients or features present in the nutritional composition. The source of fat may be derived from plants, animals, and combinations thereof. Non-limiting examples of suitable sources of fat for use in the nutritional compositions described herein include coconut oil, fractionated coconut oil, soy oil, corn oil, olive oil, safflower oil, high oleic safflower oil, high gamma-linolenic (GLA) safflower oil, medium chain triglycerides (MCT) oil, sunflower oil, high oleic sunflower oil, palm and palm kernel oils, palm olein, canola oil, marine oils, cottonseed oils, eicosapentaenoic acid, docosahexaenoic acid, gamma-linolenic acid, conjugated linolenic acid from any source, and combinations thereof.

In certain exemplary embodiments, the nutritional composition further comprises one or more functional ingredients that increase muscle protein synthesis, or decrease muscle protein degradation, or reduce muscle necrosis or apoptosis, or combinations thereof. For example, in certain exemplary embodiments, the nutritional composition further comprises a functional ingredient selected from the group consisting of: a branched-chain amino acid selected from the group consisting of leucine, isoleucine, valine, metabolites of any of the foregoing branched-chain amino acids, and combinations thereof; β-hydroxy-β-methylbutyrate (HMB); β-alanine; Vitamin D; creatine; carnitine; carnosine; anserine; taurine; α-hydroxyisovaleric acid; α-ketoglutarate; α-ketoisocaproate; α-hydroxyisocaproic acid; citrulline; arginine; and combinations thereof.

In certain exemplary embodiments, the nutritional composition comprises a branched-chain amino acid selected from the group consisting of leucine, isoleucine, valine, metabolites of any of the foregoing, and combinations thereof. Branched-chain amino acids have been shown to promote a positive protein balance in human skeletal muscle, and accordingly can be used to maintain muscle function, improve muscle function, or both.

In certain exemplary embodiments, the nutritional composition comprises β-hydroxy-β-methylbutyrate (HMB). As used herein, the terms HMB and β-hydroxy-β-methylbutyrate should be understood to include multiple forms, including, but not limited to, salts, the free acid, esters, and lactones, unless it is clear from the context that only one form is meant. HMB is a metabolite of the essential amino acid leucine and has been shown to enhance muscle mass and muscle function. One suitable form of HMB that may be utilized is the calcium salt of HMB, also designated as Ca—HMB, which is most typically the monohydrate calcium salt. The HMB used can come from any source. Calcium HMB monohydrate is commercially available from Technical Sourcing International (TSI) of Salt Lake City, Utah. Note that all amounts of HMB described herein are based on use of Ca—HMB. When referring to amounts of HMB herein, the amounts are based on the assumption that the HMB is being provided as Ca—HMB, unless specifically indicated otherwise. Other suitable forms of HMB that may be utilized include, but are not limited to, free acid, salt, anhydrous salt, ester, lactone, or other product forms that provide a bioavailable form of HMB suitable for oral administration. Non-limiting examples of suitable salts of HMB (hydrated or anhydrous) for use herein include sodium, potassium, chromium, calcium, and other non-toxic salt forms.

In certain exemplary embodiments, the nutritional composition comprises 0.4 grams to 4 grams of HMB per serving. For example, in certain embodiments, the nutritional composition comprises 0.5 grams to 3.5 grams of HMB per serving, including 0.5 grams to 2.5 grams of HMB per serving, including 1 gram to 2 grams of HMB per serving, and also including 1 gram to 1.5 grams of HMB per serving. In certain embodiments, the nutritional composition comprises 1.5 grams of HMB per serving. In certain other embodiments where the nutritional composition is a liquid, the amount of HMB in the nutritional composition may range up to 10% by weight of the nutritional composition, including from 0.01% to 10%, including from 0.1% to 5.0%, including from 0.5% to 2%, and also including from 0.4% to 1.5% by weight of the nutritional composition.

In certain exemplary embodiments, the nutritional composition comprises β-alanine. β-alanine is a naturally occurring β amino acid that is the rate-limiting precursor of carnosine. Dietary supplementation with β-alanine has been shown to increase the concentration of carnosine in muscles, delay fatigue in athletes, and increase total muscular work done. In certain exemplary embodiments, the nutritional composition comprises 0.1 grams to 10 grams of β-alanine per serving. In certain exemplary embodiments, the nutritional composition comprises 0.1 grams to 6 grams of β-alanine per serving, including 1 gram to 4 grams of β-alanine per serving, including 1 gram to 3.5 grams of β-alanine per serving, including 1 gram to 2 grams of β-alanine per serving, and also including 1.5 grams of β-alanine per serving. In certain embodiments where the nutritional composition contains β-alanine, the amount of β-alanine in the nutritional composition may range from 0.1% to 5% by weight of the nutritional composition, including from 0.1% to 2%, including from 0.1% to 1%, and also including from 0.1% to 0.5% by weight of the nutritional composition.

The β-alanine may be provided in various forms. For example, the β-alanine may be provided in free form or as a derivative (e.g., salt, ester, lactone). All amounts of β-alanine referred to herein refer to either free β-alanine or the β-alanine portion of the salt, ester, lactone, etc. Virtually any source of β-alanine is suitable for use in certain embodiments of the nutritional compositions described herein. In certain exemplary embodiments, the β-alanine is free β-alanine Free beta-alanine is commercially available from Lonza (Switzerland) and Compounds Solutions (Escondido, Calif.).

In certain exemplary embodiments, the nutritional composition comprises Vitamin D. Vitamin D is a fat soluble vitamin that is found naturally in few foods, but is synthesized in the human body upon exposure to sunlight. As used herein, "Vitamin D" refers to Vitamin D2, Vitamin D3, or combinations thereof. Dietary supplementation of Vitamin D has been shown to increase muscle mass and skeletal muscle protein synthesis. Moreover, Vitamin D may improve skeletal muscle contraction by activating one or more of protein kinase A, protein kinase B, protein kinase C, CAMK, MAPK, and vitamin D receptor pathways. In certain exemplary embodiments, the nutritional composition comprises 100 to 750 IU of Vitamin D per serving, including 200 to 600 IU, including 350 to 550 IU, and also including 500 IU of Vitamin D per serving.

In certain exemplary embodiment, the nutritional composition comprises a combination of at least one source of protein, HMB, and Vitamin D, in addition to the effective amount of EGCg. For example, in certain exemplary embodiments, the nutritional composition comprises (per serving) 15 grams to 25 grams of protein, 1 gram to 3 grams of HMB, 100 IU to 750 IU of Vitamin D, and an effective amount of EGCg. Moreover, in certain other embodiments, the nutritional composition comprises (per serving) 18 grams to 22 grams of protein, 1 gram to 2 grams of HMB, 400 IU to 600 IU of Vitamin D, and an effective amount of EGCg. In yet other embodiments, the nutritional composition comprises (per serving) 20 grams of protein, 1.5 grams of HMB, 500 IU of Vitamin D, and an effective amount of EGCg. Any of the previously discussed sources of protein (or combinations thereof) may be utilized, and the nutritional composition may be provided in any of the various product forms discussed herein.

In accordance with certain exemplary embodiments, the nutritional composition is formulated as a clear liquid having a pH ranging from 2 to 5, and also having no more than 0.5% fat by weight of the nutritional composition. The limited amount of fat contributes to the desired clarity and is compatible with a pH of 2 to 5 for certain embodiments of the nutritional composition. Typically, liquid nutritional compositions desired to be clear, or at least substantially translucent, are substantially free of fat. As used herein "substantially free of fat" refers to nutritional compositions containing less than 0.5%, including less than 0.1% fat by weight of the total composition. "Substantially free of fat" also may refer to nutritional compositions disclosed herein that contain no fat, i.e., zero fat. Furthermore, embodiments of liquid nutritional compositions that have a desired acidic pH in the range of 2 to 5, e.g., juices, fruit juices, fruit-flavored beverages, etc., typically are substantially free of fat. Liquid nutritional compositions that are both clear and have a pH ranging from 2 to 5 are also typically substantially free of fat. In certain of the preceding embodiments, the pH of the nutritional composition may be from 2.5 to 4.6, including a pH of 3 to 3.5. More specifically, in certain embodiments when the nutritional composition is a liquid, the pH of the liquid nutritional composition is 2.5 to 4.6, including 3 to 3.5, to provide a more stable pH for the EGCg. In those embodiments of the nutritional compositions that are substantially free of fat but have some amount of fat present, the fat may be present as a result of being inherently present in another ingredient (e.g., a source of protein) or may be present as a result of being added as one or more separate sources of fat.

In certain exemplary embodiments disclosed herein, the nutritional composition may further comprise other optional components or ingredients that may modify the physical, chemical, aesthetic or processing characteristics of the nutritional composition or serve as pharmaceutical or additional nutritional components. Many such optional ingredients are known or otherwise suitable for use in medical food or other nutritional products or pharmaceutical dosage forms and may also be used in the nutritional compositions disclosed herein, provided that such optional ingredients are safe for oral administration and are compatible with the essential and other ingredients in the selected product form.

Non-limiting examples of such optional ingredients include preservatives, emulsifying agents, buffers, fructooligosaccharides, galactooligosaccharides, polydextrose, prebiotics, probiotics, pharmaceutical actives, anti-inflammatory agents, additional nutrients, colorants, flavors, thickening agents and stabilizers, emulsifying agents, lubricants, and so forth.

In certain exemplary embodiments disclosed herein, the nutritional composition may further comprise at least one sweetening agent. In certain embodiments, the at least one sweetening agent is at least one sugar alcohol such as maltitol, erythritol, sorbitol, xylitol, mannitol, isolmalt, and lactitol, or at least one artificial or high potency sweetener such as acesulfame K, aspartame, sucralose, saccharin, stevia, monk fruit, tagatose, and combinations thereof. The sweetening agents, especially as a combination of a sugar alcohol and an artificial sweetener, are especially useful in formulating liquid nutritional compositions having a desirable favor profile. These sweetener combinations are especially effective in masking undesirable flavors, for example, as sometimes associated with the addition of vegetable proteins to a liquid nutritional composition. In certain exemplary embodiments disclosed herein, the nutritional composition may comprise at least one sugar alcohol with a concentration in a range from at least 0.01%, including from about 0.1% to about 10%, and also including from about 1% to about 6%, by weight of the nutritional composition. In certain exemplary embodiments disclosed herein, the nutritional composition may comprise at least one artificial sweetener with a concentration in a range from 0.01% to 5%, including from 0.05% to 3%, and also including from 0.1% to 1.0%, by weight of the nutritional composition.

A flowing agent or anti-caking agent may be included in certain embodiments of the nutritional composition to retard clumping or caking of a nutritional powder embodiment over time and to make the nutritional powder flow easily from its container. Any flowing or anti-caking agents that are known or otherwise suitable for use in a nutritional powder or product form are suitable for use herein, non-limiting examples of which include tricalcium phosphate, silicates, and combinations thereof. The concentration of the flowing agent or anti-caking agent in certain embodiments of the nutritional composition disclosed herein varies depending upon the product form, the other selected ingredients, the desired flow properties, and so forth, but most typically range from 0.1% to 4% by weight of the nutritional composition, including from 0.5% to 2% by weight of the nutritional composition.

In certain exemplary embodiments, the nutritional composition may comprise a stabilizer. Any stabilizer that is known or otherwise suitable for use in a nutritional composition is also suitable for use herein, some non-limiting examples of which include gums such as xanthan gum. In certain exemplary embodiments disclosed herein, the stabilizer may represent from 0.1% to 5% by weight of the nutritional composition, including from 0.5% to 3%, and also including from 0.7% to 1.5% by weight of the nutritional composition.

In certain exemplary embodiments, the nutritional composition comprises any of a variety of vitamins or related nutrients, non-limiting examples of which include vitamin A, vitamin C, vitamin E, vitamin D2, vitamin D3, vitamin A palmitate, vitamin E acetate, vitamin C palmitate (ascorbyl palmitate), vitamin K, thiamine, riboflavin, pyridoxine, vitamin B12, carotenoids (e.g., beta-carotene, zeaxanthin, lutein, lycopene), niacin, folic acid, pantothenic acid, biotin, vitamin C, choline, inositol, salts and derivatives thereof, and combinations thereof. In yet other embodiments, the nutritional composition comprises any of a variety of additional minerals, non-limiting examples of which include calcium, selenium, potassium, iodine, phosphorus, magnesium, iron, zinc, manganese, copper, sodium, molybdenum, chromium, chloride, and combinations thereof.

In certain exemplary embodiments, the nutritional composition optionally includes one or more masking agents to reduce or otherwise obscure the development of any residual bitter flavors and after taste in the nutritional compositions over time. Suitable masking agents include natural and artificial sweeteners; sodium sources such as sodium chloride; hydrocolloids such as guar gum, xanthan gum, carrageenan, and gellan gum; and combinations thereof. The amount of masking agent in certain embodiments of the nutritional composition may vary depending upon the particular masking agent selected, other ingredients in the formulation, and other formulation or product target variables. Such amounts, however, most typically range from 0.1% to 3% by weight of the nutritional composition, including form 0.15% to 3%, and also including from 0.2% to 2.5% by weight of the nutritional composition.

The various exemplary embodiments of the nutritional composition described herein may be prepared by any process or suitable method (now known or known in the future) for making a selected product form, such as a nutritional solid or a nutritional liquid. Many such techniques are known for any given product form such as nutritional liquids or nutritional powders and can readily be applied by one of ordinary skill in the art to the various embodiments of the nutritional composition described herein.

In one suitable manufacturing process for liquid nutritional compositions, for example, at least three separate slurries are prepared, including a protein-in-fat (PIF) slurry, a carbohydrate-mineral (CHO-MIN) slurry, and a protein-in-water (PIW) slurry. The PIF slurry is formed by heating and mixing an oil (e.g., canola oil, corn oil) and then adding an emulsifier (e.g., lecithin), fat soluble vitamins, and a portion of the total protein (e.g., milk protein concentrate) with continued heat and agitation. The CHO-MN slurry is formed by adding with heated agitation to water: minerals (e.g., potassium citrate, dipotassium phosphate, sodium citrate), trace and ultra trace minerals (TM/UTM premix), thickening or suspending agents (e.g., gellan, carrageenan).

The resulting CHO-MIN slurry is held for 10 minutes with continued heat and agitation before adding additional minerals (e.g., potassium chloride, magnesium carbonate, potassium iodide), or carbohydrates (e.g., fructooligosaccharide, sucrose, corn syrup), or combinations thereof. The PIW slurry is then formed by mixing with heat and agitation the remaining protein.

In accordance with this process, the three resulting slurries are blended together with heated agitation and the pH adjusted to the desired range (e.g., 6.6 to 7) after which the nutritional composition is subjected to high-temperature short-time (HTST) processing. The nutritional composition is heat treated, emulsified, homogenized, and cooled during HTST. Water soluble vitamins and ascorbic acid are added (if applicable), the pH is again adjusted (if necessary), flavors are added, and any additional water can be added to adjust the solids content to the desired range. The EGCg or source of EGCg (e.g., a green tea extract) is prepared as a solution (e.g., 1% (w/w)) by adding to water and agitating for 0-24 hours. The solution of EGCg is added to the composition containing the other ingredients and is agitated for a period of time (e.g., 5-60 minutes) to ensure homogeneous distribution of the EGCg in the composition. The agitation associated with the preparation of the solution containing EGCg, along with the addition of the EGCg solution to the other ingredients, may take place at 4° C. to 50° C. At this point, the liquid nutritional composition may be packaged and sterilized according to any suitable sterilization technique, such as aseptic, retort, or hot-fill sterilization.

A nutritional powder, such as a spray dried nutritional powder or dry blended nutritional powder, may be prepared by any collection of known or otherwise effective technique, suitable for making and formulating a nutritional powder. For example, when the nutritional powder is a spray dried nutritional powder, the spray drying step may likewise include any spray drying technique that is known for or otherwise suitable for use in the production of nutritional powders. Many different spray drying methods and techniques are known for use in the nutrition field, all of which are suitable for use in the manufacture of the spray dried nutritional powders herein.

One method of preparing the spray dried nutritional powder comprises forming and homogenizing an aqueous slurry or liquid comprising predigested fat, and optionally protein, carbohydrate, and other sources of fat, and then spray drying the slurry or liquid to produce a spray dried nutritional powder. The method may further comprise the step of spray drying, dry blending, or otherwise adding additional nutritional or functional ingredients, including any one or more of the ingredients described herein, to the spray dried nutritional powder.

Other suitable methods of making nutritional products are described, for example, in U.S. Pat. No. 6,365,218 (Borschel, et al.), U.S. Pat. No. 6,589,576 (Borschel, et al.), U.S. Pat. No. 6,306,908 (Carlson, et al.), U.S. Pat. Appl. No. 20030118703 A1 (Nguyen, et al.), which descriptions are incorporated herein by reference to the extent that they are consistent herewith.

The exemplary methods disclosed herein include administering, or providing, to a subject in need thereof an amount of EGCg effective to achieve at least one of the following: (1) an increase in the level of muscle VEGF; (2) an increase in muscle vasculature; (3) an increase in muscle blood flow; (4) a decrease in myostatin levels; and (5) inhibition of myostatin activity; and thereby decrease muscle function decline, improve muscle function, or both. As explained elsewhere herein, the increase in intramuscular VEGF that was identified via the studies presented in the Examples herein was unexpected since EGCg has been previously identified as an anti-cancer agent due to its ability to downregulate VEGF expression and thus inhibit angiogenesis and subsequent vascularization of pre-tumorogenic tissue. Moreover, the decrease in myostatin levels illustrated in the Examples, particularly intramuscular myostatin levels, can reduce myostatin associated signaling in the muscle, which may promote muscle cell differentiation and proliferation, as well as increase muscle protein synthesis, decrease muscle protein degradation, or combinations thereof. In addition, the amount of EGCg administered, or provided, to a subject in need thereof according to the methods disclosed herein is also effective to reduce intramuscular levels of interleukin-1-alpha (IL1A) in the subject.

IL1A is a pro-inflammatory cytokine released by T cells, B cells, macrophages, and other inflammatory mononuclear cells. Increased levels of IL1A have been observed in the skeletal muscle of patients having inflammatory muscle diseases, such as polymyositis and dermatomyositis. In addition, IL1A levels are elevated in cachexic patients, and IL1A has been shown to directly stimulate muscle protein breakdown. Accordingly, a decrease in the level of intramuscular IL1A effected by the administration of EGCg according to the exemplary methods described herein can reduce muscle inflammation and catabolism, and thereby decrease muscle function decline, improve muscle function, or both.

In certain exemplary embodiments, the subject in need thereof is a human. In certain other exemplary embodiments, the subject in need thereof is an elderly human. In certain exemplary embodiments, the subject in need thereof is a subject who is experiencing muscle function decline; a subject in need of muscle function improvement by virtue of having one or more of sarcopenia, cachexia, diabetes, peripheral arterial disease, intermittent claudication, ischemia reperfusion injury, or chronic obstructive pulmonary disease (COPD); a subject who is bedridden or otherwise immobile (either temporarily or permanently) and suffers from muscle disuse; or combinations thereof. In certain exemplary embodiments, the subject in need thereof is a subject having or at risk of having muscle function decline. Symptoms of muscle function decline include, but are not limited to, decreased muscle growth, decreased muscle oxygenation, muscle inflammation, and increased muscle catabolism. Such symptoms may manifest as a result of aging, sarcopenia, cachexia, inactivity, immobility (e.g., bed rest or due to a cast), diabetes, chronic disease (e.g., COPD, end-stage renal disease), peripheral arterial disease, intermittent claudication, ischemia reperfusion injury, or combinations thereof. In certain other exemplary embodiments, the subject in need thereof is hospitalized. In yet other exemplary embodiments, the subject in need thereof is undergoing rehabilitation subsequent to a period of injury, disease, surgery, immobilization, hospitalization, and combinations thereof. In still other exemplary embodiments, the subject in need thereof has elevated myostatin levels.

As used herein, the phrase "decreasing muscle function decline in a subject in need thereof" should be understood to include one or more of reducing the rate of muscle function decline, maintaining muscle function, or improving muscle function. As noted above, muscle function includes at least one of muscle mass and muscle strength. In addition, "decreasing muscle function decline" or "improving muscle function" should be understood to include one or more of increasing muscle growth, increasing muscle oxygenation, increasing muscle endurance, reducing muscle inflammation, decreasing muscle catabolism, increasing muscle vasculature (i.e., increasing vascularization and capillarization), increasing intramuscular blood flow, increasing muscle mass, and increasing muscle strength.

Muscle function in a subject may be evaluated by a wide variety of methods. For example, muscle function in terms of muscle mass in a subject may be determined by using any known or otherwise effective technique that provides muscle area, volume, or mass, such as DEXA, or using visual or imaging techniques such as MRI or CT scans. In addition, muscle function in a subject in terms of muscle strength can be quantitatively measured using acute tests of maximum force, time-dependent tests of muscle endurance, time dependent tests of muscle fatigue, time dependent tests of muscle endurance and fatigue, and combinations thereof. Furthermore, muscle function in a subject may be measured by using a grip meter, by evaluating lower extremity strength using equipment to measure isokinetic knee extensor or knee flexor strength, and by measuring gait and balance (e.g., Tinetti Gait and Balance test).

In certain exemplary embodiments, muscle function in a subject may be measured by determining the levels of one or more of VEGF, IL1A, and myostatin in a biological sample obtained from the subject. For example, in certain exemplary embodiments, a muscle tissue sample is obtained from the subject (e.g., via needle biopsy), and is assayed to measure myostatin levels. Of course, the muscle tissue sample may also be assayed to measure VEGF levels, IL1A levels, or both. In certain exemplary embodiments, the biological sample is a blood sample obtained from the subject, which is then assayed to measure circulating levels of myostatin, VEGF, IL1A, and combinations thereof. In certain exemplary embodiments, the blood sample is a whole blood sample, or a sample of a blood fraction including, but not limited to, serum and plasma. Any number of assays known to those of skill in the art may be used to measure the levels of one or more of VEGF, IL1A, and myostatin in the biological sample. For example, the levels of VEGF, IL1A, and myostatin in the biological sample may be measured by assays such as, for example, ELISA, western blot, quantitative reverse transcription polymerase chain reaction, and RNase protection assay.

As discussed above, "decreasing muscle function decline" or "improving muscle function" includes increasing muscle vasculature (i.e., increasing vascularization and capillarization) and increasing intramuscular blood flow. Intramuscular blood flow can be non-invasively measured using doppler ultrasound methods, the particulars of which would be known and understood by those of skill in the art, and as described in Olive et al., *Dynamic Medicine* (2002), Vol. 1 (7 pages). Moreover, it is also possible to measure microvascular blood volume in muscles using real time ultrasound imaging (Sjoberg et al., *Am J Physiol Heart Circ Physiol* (2011), Vol. 301, pp. H450-H458). In addition, intramuscular blood flow can measured by infusing indocyanine green (ICG) in femoral and wrist veins for spectrophotometrical determination (Beckman Coulter, Fullerton, Calif.) at 805 nm (Timmerman et al., *J Clin Endocrinol Metab* (2010), Vol. 95, No. 8, pp. 3848-3857). Those of skill in the art will appreciate that other methods of measuring intramuscular blood flow may be utilized.

As previously discussed, "decreasing muscle function decline" as used herein also refers, in certain exemplary embodiments of the methods disclosed herein, to the maintenance of muscle function in the subject. In this context, maintenance of muscle function in the subject refers to retaining an amount of muscle function that corresponds to a measurement of the muscle function of the subject prior to initiating the methods disclosed herein, or a percentage thereof. Accordingly, in various embodiments of the methods disclosed herein, administering an amount of EGCg (or a nutritional composition containing EGCg) effective to increase the level of muscle VEGF, to decrease myostatin levels, or both results in maintaining 100% of the muscle function of the subject, or in other embodiments lesser amounts. For example, in certain exemplary embodiments, the method results in maintaining at least 50% muscle function, 60% muscle function, 70% muscle function, 80% muscle function, 90% muscle function, 95% muscle function, or any amounts ranging from 50% to 100%, including 50% to 80%, 50% to 90%, 60% to 80%, and 60% to 90%. In certain exemplary embodiments, muscle function decline is entirely prevented; in other words, the subject maintains 100% muscle function, or even increases muscle function. Generally, when muscle function in a subject is "maintained" by more than 100%, this result is described herein as an improvement in muscle function.

Various embodiments of the methods disclosed herein result in an improvement of muscle function in a subject. The terms "improve," "improves," "improvement," and "improving" when used in connection with muscle function refers to an increase in muscle function, or alternatively, maintenance of muscle function above 100% as compared to a period of time before initiation of the methods disclosed herein. For example, in certain exemplary embodiments, administering an amount of EGCg effective to increase the level of muscle VEGF, to decrease myostatin levels, or both can increase the subject's muscle function by at least 10%, such as 10% to 100%. In certain exemplary embodiments, muscle function can be improved by 1%, 5%, 10%, 20%, 30%, 40%, 50%, 60%, 70%, 80%, 90%, 95%, or 100%.

In terms of measuring an improvement in muscle function, a decrease in muscle function decline, or maintenance of muscle function, a first measurement of the muscle function of the subject is performed prior to initiating the methods disclosed herein. In certain embodiments of the methods disclosed herein, the first measurement is performed a week (e.g., 1-7 days or 7 days) before initiation of the methods disclosed herein. Next, a second measurement of the muscle function of the subject is performed at some time point after initiating the methods disclosed herein, and the second measurement is compared to the first measurement. The comparison of the second measurement to the first measurement may not show immediate results using the aforementioned measurement techniques. The resulting effect may take days, weeks, or months of administration of EGCg (or compositions containing EGCg) according to the dosages and in the intervals previously described herein to obtain the stated measurable muscle function results described above. For chronic loss of muscle or muscle function such as that associated with sarcopenia or cachexia, administration for several weeks (e.g., 4-8 weeks) to months (e.g., 3-12 months) may be needed to achieve the desired effect. For acute loss of muscle or muscle function due to, for example, immobilization or hospitalization, regular administration of EGCg (or compositions containing EGCg) for 3-10 days may be sufficient to achieve the desired effect. In certain exemplary embodiments according to the methods disclosed herein, the amount of time between the first measurement of muscle function and the second measurement of muscle function is two weeks, one month, two months, six months, or more. In certain exemplary embodiments, for purposes of determining the effects of the methods of administering EGCg as disclosed herein, a 3-12 month test period of regular administration of the EGCg may be used. In certain other exemplary embodiments, for purposes of determining the effects of the methods of administering EGCg as disclosed herein, a 2 week to 3 month test period of regular administration of the EGCg may be used.

As discussed above, a decrease in muscle function decline or an improvement in muscle function in a subject may be measured in a variety of ways. For example, a biological sample may be obtained from the subject (e.g., a muscle tissue sample via needle biopsy) prior to initiating the methods disclosed herein and again at a time point after initiating the methods disclosed herein. The biological samples may then be assayed to measure and compare the levels of one or more of myostatin, VEGF, and IL1A. In addition, an animal study (e.g., according to Example 3 or a similar study) may be used to show that administration of EGCg (or a composition containing EGCg) according to the methods disclosed herein results in a decrease in muscle function decline or an improvement in muscle function.

EXAMPLES

The following examples illustrate certain embodiments of the exemplary methods and compositions disclosed herein. The examples are given solely for the purpose of illustration and are not to be construed as limitations of the present disclosure, as many variations thereof are possible without departing from the spirit and scope of the disclosure.

Example 1

Example 1 illustrates an exemplary embodiment of a nutritional composition described herein. All ingredient amounts listed in Example 1 are listed as kilogram per 1000 kg batch of product, unless otherwise indicated. Example 1 shows an exemplary formulation of a emulsion-type liquid nutritional composition containing protein, carbohydrates, and fat and has a pH in the range of 6.6 to 7. Assuming a density of 1.075 g/mL and a serving size of about 237 mL (about 8 fl. oz.), a nutritional composition according to the formulation shown in Example 1 has about 177 mg of EGCg per serving. In addition, the nutritional composition includes 11 g of protein per serving (or about 0.047 g/mL), 40 g of carbohydrate per serving (or about 0.17 g/mL), and 6 g of fat per serving (or about 0.24 g/mL).

EXAMPLE 1

| INGREDIENTS | Amount (kg/1000 kg) |
|---|---|
| Water | Quantity Sufficient |
| EGCg-containing Green Tea Extract[1] | 1.390 |
| Sucrose | 89.1 |
| Maltodextrin | 69.1 |
| Milk Protein Concentrate | 38.6 |
| Soy Oil | 13.3 |
| Canola Oil | 5.3 |
| Soy Protein Concentrate | 4.7 |
| Corn Oil | 4.1 |
| Potassium Citrate | 2.7 |
| Natural and artificial Vanilla Flavor | 2.0 |
| Magnesium Phosphate Dibasic | 1.9 |
| Sodium Citrate | 1.6 |
| Soy Lecithin | 1.4 |
| Tricalcium Phosphate | 1.3 |
| Magnesium Chloride | 1.2 |
| Sodium Chloride | 0.718 |

-continued

EXAMPLE 1

| INGREDIENTS | Amount (kg/1000 kg) |
| --- | --- |
| Choline Chloride | 0.480 |
| Ascorbic Acid | 0.469 |
| Carrageenan | 0.450 |
| Ultra Trace Mineral/Trace Mineral Premix | 0.364 |
| Potassium Hydroxide (Processing aid) | 0.323 |
| Potassium Chloride | 0.308 |
| Vitamin Premix[2] | 0.1465 |
| Potassium Iodide | 0.000207 |

[1]SUNPHENON® 90D (available from Taiyo International, Inc. of Minneapolis, Minnesota) is a green tea extract that contains approximately 50% by weight of EGCg, i.e., 1.390 kg of green tea extract contains approximately 0.695 kg EGCg.
[2]Vitamin premix includes one or more of the following: dl-Alpha-Tocopheryl Acetate, Vitamin A Palmitate, Phylloquinone, Vitamin D3, Niacinamide, d-Calcium Pantothenate, Thiamine Chloride Hydrochloride, Pyridoxine Hydrochloride, Riboflavin, Folic Acid, Biotin, Cyanocobalamin, etc.

Example 2

Example 2 illustrates an exemplary embodiment of a nutritional composition described herein. All ingredient amounts listed in Example 2 are listed as kilogram per 1000 kg batch of product, unless otherwise indicated. Example 2 shows an exemplary formulation of a clear-type liquid nutritional composition that is substantially free of fat and having a pH in the range of 3 to 3.5. Assuming a density of 1.05 g/mL and a serving size of about 296 mL (about 10 fl. oz.), a nutritional composition made according to the formulation shown in Example 2 has about 188 mg of EGCg per serving. In addition, the nutritional composition includes 9 g of protein per serving (or about 0.0304 g/mL), 35 g of carbohydrate per serving (or about 0.118 g/mL), 0 g of fat per serving, and an energy content of 180 kcal per serving (or about 0.61 kcal/mL).

EXAMPLE 2

| INGREDIENTS | Amount (kg/1000 kg) |
| --- | --- |
| Water | Quantity Sufficient |
| Sucrose | 50.7 |
| Corn syrup solids | 61.3 |
| Acidified Whey Protein Isolate | 35.7 |
| Citric Acid | 2.00 |
| Flavoring | 2.00 |
| EGCg-containing Green Tea Extract[1] | 1.212 |
| Ascorbic Acid | 0.535 |
| Liquid Sucralose (25%) | 0.275 |
| Ultra Trace Mineral/Trace Mineral Premix | 0.230 |
| Vitamin Premix[2] | 0.219 |
| Acesulfame Potassium | 0.110 |
| Antifoam processing aid (non-silicone) | 0.060 |
| Coloring | 0.0589 |
| Natural and Artificial Peach Flavor | 2.0 |
| Folic Acid | 0.0013 |
| Potassium Iodide | 0.000204 |

[1]SUNPHENON® 90D, which is a green tea extract that contains approximately 50% by weight of EGCg, i.e., 1.212 kg of green tea extract contains approximately 0.606 kg EGCg.
[2]Vitamin premix includes one or more of the following: dl-Alpha-Tocopheryl Acetate, Vitamin A Palmitate, Phylloquinone, Vitamin D3, Niacinamide, d-Calcium Pantothenate, Thiamine Chloride Hydrochloride, Pyridoxine Hydrochloride, Riboflavin, Folic Acid, Biotin, Cyanocobalamin, etc.

Example 3

Example 3 illustrates the effect of 8 weeks of dietary EGCg supplementation on skeletal muscle biomarkers in the aged Sprague Dawley (SD) rat model of sarcopenia. More particularly, gastrocnemius muscle lysates of aged SD rats administered EGCg were analyzed for changes in various skeletal muscle biomarkers.

In Vivo Study 1—Aged (25 Months Old) Vs. Adult (13 Months Old)-Male SD rats (12 months old; adult rats; Dataset A) and male SD rats (24 months old; aged rats; Dataset B) were purchased from Harlan (Indianapolis, Ind.). The rats were single-housed in cages with hardwood chip bedding and were exposed to a 12-hour light cycle. At receipt, rats had ad libitum access to natural chow (Teklad Global 18% Protein Rodent Diet, catalog #2018S, Harlan) and water during adaptation to the animal facility. Adult rats (Dataset A) were 13 months old at the time of sacrifice, and aged rats (Dataset B) were 25 months old at the time of sacrifice. The right gastrocnemius muscle of the rats were collected and flash-frozen on liquid nitrogen.

In Vivo Study 2—EGCg Supplementation-Male SD rats (19 months old) were purchased from Harlan (Indianapolis, Ind.). The rats were single-housed in cages with hardwood chip bedding and were exposed to a 12-hour light cycle. At receipt, rats had ad libitum access to purified diet AIN-93M (Research Diets, #D10012M) and water during adaptation to the animal facility. Subsequently, the rats were given ad libitum access to AIN-93M diet supplemented with EGCg-rich (>95%) Teavigo® at 200 mg/kg body weight (Dataset C) for 8 weeks.

In Vivo Study 3—EGCg Supplementation-Male SD rats (19 months old) were purchased from Harlan (Indianapolis, Ind.). The rats were single-housed in cages with hardwood chip bedding and were exposed to a 12-hour light cycle. At receipt, rats had ad libitum access to purified diet AIN-93M (Research Diets, #D10012M) and water during adaptation to the animal facility. Subsequently, the rats were given ad libitum access to either AIN-93M diet (Dataset D) or AIN-93M diet supplemented with EGCg-rich (>95%) Teavigo® at 50 mg/kg body weight (Dataset E) for 8 weeks.

Preparation of Muscle Lysates-Whole gastrocnemius muscles were collected from euthanized rats (Dataset A, Dataset B, Dataset C, Dataset D, and Dataset E) and flash-frozen on liquid nitrogen and stored in aluminum foil at −80° C. Subsequently, the gastrocnemius muscle samples were partially thawed on dry ice. Approximately 200 mg of tissue was obtained from each muscle sample by mechanical biopsy punch. The specimens were quickly pulverized on liquid nitrogen and transferred to a 15 mL conical tube and weighed. A mild, detergent-free lysis buffer (9×) was added to the dried specimen in the conical tube. 9× Lysis buffer (50 mM Tris.HCl, 2 mM EDTA, pH 7.4/NaOH) was supplemented with a mammalian protease inhibitor cocktail (Sigma-Aldrich, Inc.) at a 1:200 dilution and stored on ice. The specimens were then vortexed for 10 seconds ahead of homogenization at 25×1000 rpm for approximately 10 seconds. The lysate was vortexed again for 10 seconds and transferred to a 1.5 mL tube. Lysates were centrifuged/clarified for 5 minutes at 11000 rpm at 4° C. in a standard table-top Eppendorf centrifuge. Supernatant (1 mL) was aliquotted to a 2 mL cryotube and stored at −80° C. Lysates were analyzed by Myriad Rules Based Medicine (Austin, Tex.) on the RodentMAP® v.2.0 Antigens and Rat META-BOLIC® multi-analyte profiling platforms.

Figure 1B:
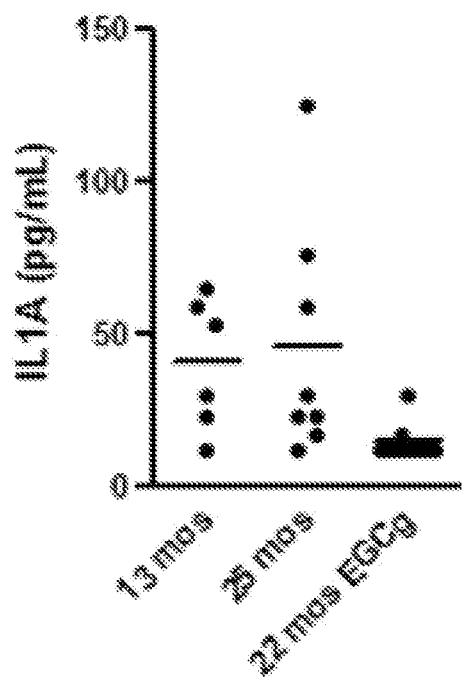
Figure 2:
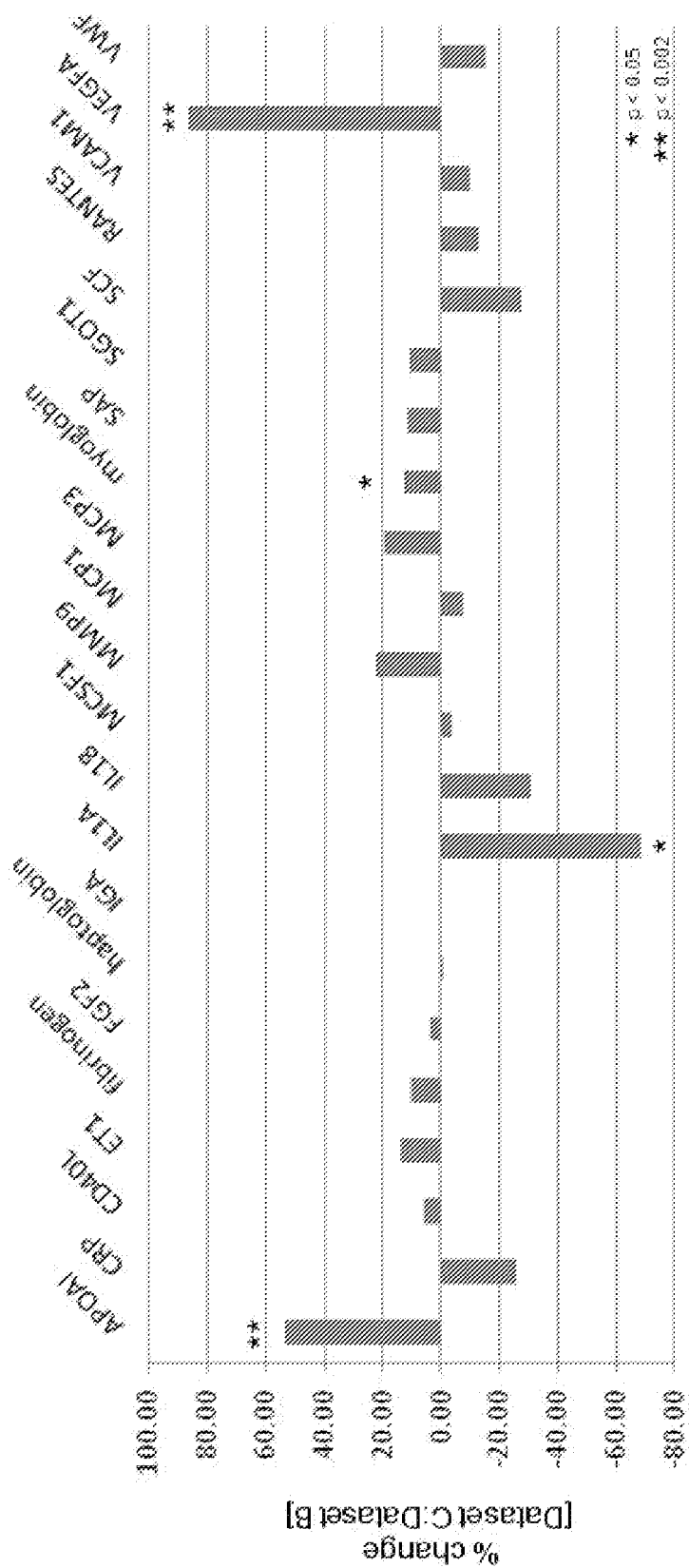
FIG. 2 shows the effects of dietary EGCg supplementation on aged SD rat gastrocnemius intramuscular markers.

Results-As seen in FIGS. 1-2 and Tables 1 and 2 below, 22 month old rats that received EGCg supplementation (200 mg/kg body weight; Dataset C) exhibited increased intramuscular levels of VEGF (+86%, p<0.001) and reduced intramuscular levels of IL1A (−69%, p=0.022), as compared to 25 month old rats (Dataset B) that did not receive EGCg supplementation.

TABLE 1

| | Analytical Experiment[1] | | | | |
| --- | --- | --- | --- | --- | --- |
| | Quantitative Assay I | | | Quantitative Assay II | |
| Data Label | Dataset A | Dataset B | Dataset C | Dataset D | Dataset E |
| In Vivo Study[2] | 1 | | 2 | 3 | |
| Age at Sacrifice | 13 mos | 25 mos | 22 mos | 22 mos | 22 mos |
| Diet | Control | Control | EGCg[3] | Control | EGCg[3] |
| EGCg dose | — | — | 200 mg/kg bw | — | 50 mg/kg bw |
| VEGF (pg/mL) | 135 | 123 | 229 | 506 | 479 |
| % change | | | | | |
| Dataset C/Dataset B | | | +86% (P < 0.001) | | |
| Dataset E/Dataset D | | | | | −5% (n.s.) |
| IL1A (pg/mL) | 40.3 | 46.6 | 14.3 | 31.9 | 28.0 |
| % change | | | | | |
| Dataset C/Dataset B | | | −69% (P = 0.022) | | |
| Dataset E/Dataset D | | | | | −12% (n.s.) |

[1]Quantitative Assays I and II were performed on separate dates, independent of one another.
[2]Each in vivo study is a separate experiment, conducted at separate times, with each study having its own controls. Control diet muscle samples from In Vivo Study 2 were not analyzed.
[3]Control diet supplemented with Teavigo ® (>95% EGCg) (DSM, Netherlands) at the dosage indicated.
n.s. = not significant

TABLE 2

| | Control Diets Dataset B (25 mos.) v. Dataset A (13 mos.) | | Dataset C (EGCg Supplemented - 22 mos.) v. Dataset B (25 mos.) | |
| --- | --- | --- | --- | --- |
| Marker | Serum | Muscle | Serum | Muscle |
| IL1A | −39% (n.s.) | +13% (n.s.) | −8% (n.s.) | −69% |
| VEGF | +13% (n.s.) | −9% (n.s.) | −15% (n.s.) | +86% | n.s. = not significant

As noted, 22 month old rats supplemented with EGCg (200 mg/kg body weight; Dataset C) exhibited increased intramuscular levels of VEGF and decreased intramuscular levels of IL1A as compared to Dataset B. These particular proteins are associated with biological pathways that promote muscle function. For example, VEGF promotes muscle vasculature (increased muscle blood flow) and muscle oxygenation via angiogenesis. Moreover, increased levels of IL1A have been shown to directly stimulate muscle protein breakdown. Accordingly, the data support a finding that EGCg supplementation will decrease muscle function decline, improve muscle function, or both by increasing intramuscular levels of VEGF, decreasing intramuscular levels of IL1A, and combinations thereof, and particularly by increasing intramuscular levels of VEGF.

Example 4

Example 4 illustrates the effect of 8 weeks of dietary EGCg supplementation in the aged Sprague Dawley (SD) rat model of sarcopenia. More particularly, the level of myostatin in gastrocnemius muscle lysates of young SD rats ("young"), aged SD rats ("old"), and aged SD rats administered EGCg ("old-EGCg") was analyzed and compared.

In Vivo Study—EGCg Supplementation-Male SD rats (20 months old) were purchased from Harlan (Indianapolis, Ind.). The rats were single-housed in cages with hardwood chip bedding and were exposed to a 12-hour light cycle. For 1 week, rats had ad libitum access to purified diet AIN-93M (Research Diets, #D10012M) and water during adaptation to the animal facility. The AIN-93M diet typically comprises about 13% (by weight) protein, about 73% (by weight) carbohydrate, and about 4% (by weight) fat, and has an energy content of about 3.77 kcal/gram. Subsequently, the rats were given ad libitum access to AIN-93M diet supplemented with EGCg (>95%) (Teavigo, DSM) at 200 mg/kg body weight (n=12) ("old-EGCg" or "EGCg supplemented") or control AIN-93 diet (n=11) ("old" or "Control") for 8 weeks.

Preparation of Muscle Lysates-Whole gastrocnemius muscles were collected from euthanized rats, weighed, and flash-frozen on liquid nitrogen and stored in aluminum foil at −80° C. Subsequently, the gastrocnemius muscle samples were partially thawed on dry ice. Approximately 200 mg of tissue was obtained from each muscle sample by mechanical biopsy punch. The specimens were quickly pulverized on liquid nitrogen and transferred to a 15 mL conical tube and weighed. A mild, detergent-free lysis buffer (9×) was added to the dried specimen in the conical tube. 9× Lysis buffer (50 mM Tris.HCl, 2 mM EDTA, pH 7.4/NaOH) was supplemented with a mammalian protease inhibitor cocktail (Sigma-Aldrich, Inc.) at a 1:200 dilution and stored on ice. The specimens were then vortexed for 10 seconds ahead of homogenization at 25×1000 rpm for approximately 10 seconds. The lysate was vortexed again for 10 seconds and transferred to a 1.5 mL tube. Lysates were centrifuged/clarified for 5 minutes at 11000 rpm at 4° C. in a standard table-top Eppendorf centrifuge. Supernatant (1 mL) was aliquotted to a 2 mL cryotube and stored at −80° C.

Western blot analysis was carried out using anti-myostatin antibodies (Anti-GDF8/Myostatin antibody-Cat.# ab996-Abcam). Briefly, samples of cytosolic protein (10-15 µg) were resolved by 10% sodium dodecylsulphate-polyacrylamide gel electrophoresis (SDS-PAGE) at 180 V for approximately 1 hour, followed by transference onto 0.45 µm nitrocellulose membranes, which were then blocked with 5% Marvel in Tris-buffered saline, pH 7.5, at 4° C. overnight. Anti-myostatin antibody (1:50 dilution) and secondary antibody (1:1000 dilution) was used. Incubation with primary antibody was carried out overnight, secondary antibody for 1 hour, and development was by ECL Reagent (GE Health Care Sciences) chemiluminescent detection. Blots were scanned by densitometry to quantitate differences. Young muscle lysates were prepared from 6 month old SD rats and were used as the young control in the western blots to compare myostatin levels of old rats and young rats.

Results-Table 3 shows a comparison of average gastrocnemius wet weights from Control rats and EGCg supplemented rats at the end of the 8-week feeding period. As can be seen, there was a significant increase in gastrocnemius muscle wet weight in the EGCg supplemented rats compared to the Control rats. Accordingly, the data indicates that EGCg is effective for attenuating muscle atrophy due to sarcopenia.

TABLE 3

| Group | Muscle Wet Weight (grams) | % change from control |
| --- | --- | --- |
| Control | 2.85 ± 0.06 | — |
| EGCg Supplemented | 3.00 ± 0.03* | +5.12% |

*p < 0.05, compared to Control (t-test)

Figure 3:
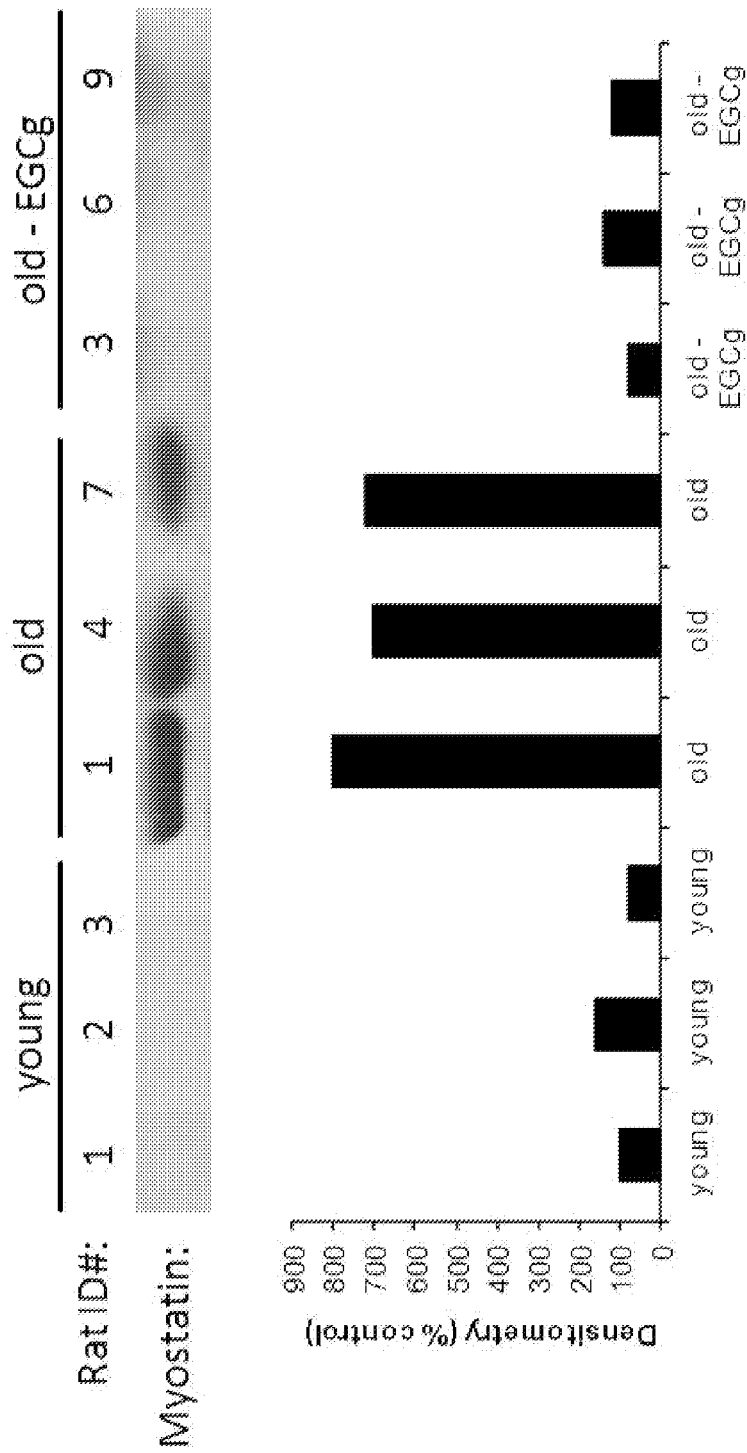
FIG. 3 shows a combination of bar graphs and the results of a western blot analysis of gastrocnemius muscle lysates showing a decrease in myostatin levels in EGCg-supplemented Sprague Dawley rats as compared to controls.

FIG. 3 and Table 4 show the western blot results from randomly selected rats from each group used in the study. Myostatin levels in muscles from three young rats (6 months old; "young"), three aged rats (22 months old; "old"), and three aged EGCg supplemented rats (22 months old; "old-EGCg") are illustrated. The results indicate that the "old-EGCg" rats exhibited decreased levels of intramuscular myostatin protein, as compared to the "old" rats that did not receive EGCg supplementation. Accordingly, the results show that EGCg inhibited expression of myostatin in vivo. Moreover, the myostatin levels of the "old-EGCg" rats were similar to the myostatin levels of the "young" rats. Therefore, the data support a finding that EGCg supplementation decreases intramuscular levels of myostatin, and thereby attenuates muscle function decline, attenuates loss of muscle mass, and thus improves overall functionality.

TABLE 4

| GROUP | Rat ID# | Myostatin (% cage control) |
| --- | --- | --- |
| Young | 1 | 100 |
|  | 2 | 160 |
|  | 3 | 80 |
| Old | 1 | 800 |
|  | 4 | 700 |
|  | 7 | 720 |
| Old-EGCg | 3 | 80 |
|  | 6 | 140 |
|  | 9 | 120 |

Example 5

Example 5 illustrates the effect of EGCg on expression of myostatin in serum starved $C_2C_{12}$ myotubes. $C_2C_{12}$ myoblasts were passaged in DMEM supplemented with 10% fetal calf serum (FCS), 1% glutamine, and 1% penicillin-streptomycin under an atmosphere of 10% $CO_2$ in air at 37° C. When the myoblasts reached about 80% confluency, they were differentiated into myotubes in DMEM containing 2% horse serum (HS), with medium changes every 2 days. Differentiation was complete in 5-7 days, and the myotubes remained viable for a further 4-5 days.

To induce protein degradation in the myotubes, HS-supplemented DMEM media was replaced with DMEM medium without any serum for 24 hrs, while the negative control group of myotubes ("NC") was not deprived of serum (i.e., the NC group was re-fed with DMEM media containing 2% HS). Myotubes were treated with EGCg (10 µM and 25 µM) over this serum starvation period. Western blot analysis was carried out on cell lysates as described in Example 4.

Figure 4:
FIG. 4 shows a combination of bar graphs and the results of a western blot analysis of $C_2C_{12}$ myotube lysates showing a decrease in myostatin levels in serum starved EGCg-supplemented $C_2C_{12}$ myotubes.
Figure 4:
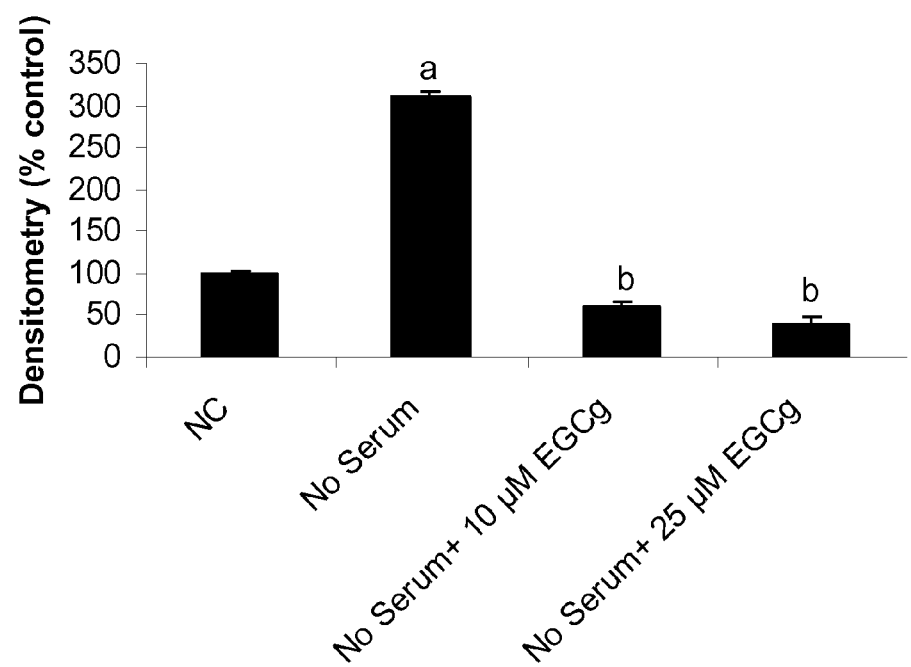
Figure 4:

FIG. 4 and Table 5 illustrate the expression of myostatin in the non-serum starved control cells ("NC"), serum starved control cells ("No Serum"), and EGCg treated serum starved cells ("No Serum+10 µM EGCg" and "No Serum+25 µM EGCg"). The densitometric analysis was based on three separate blots. Results are expressed as mean plus S.E.M., and statistical analysis between groups was determined by one-way ANOVA followed by Tukey's test. The difference from the "NC" group is indicated as "a" ($p<0.01$), while the difference from the "No Serum" group is indicated as "b" ($p<0.01$).

As seen in FIG. 4 and Table 5, the EGCg treated groups had significantly lower myostatin levels as compared to the "No Serum" group. These results are consistent with the effects of EGCg on myostatin levels in vivo, as observed in Example 3 above. Accordingly, the data support a finding that EGCg supplementation will decrease muscle function decline, improve muscle function, or both by decreasing myostatin levels.

TABLE 5

| GROUP | Myostatin (% control) |
| --- | --- |
| NC (non-serum starved control cells) | 100 |
| No Serum (serum starved control cells) | 315 |
| No Serum + 10 µM EGCg (EGCg treated serum starved cells) | 55 |
| No Serum + 25 µM EGCg (EGCg treated serum starved cells) | 43 |

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. Also, to the extent that the terms "in" or "into" are used in the specification or the claims, it is intended to additionally mean "on" or "onto," respectively.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative methods and compositions, and illustrative examples shown and described. Accordingly, departures may be made from such details without departing from the spirit or scope of the general inventive concept.

What is claimed is:

1. A method of decreasing a myostatin level in a subject in need thereof, the method comprising administering epigallocatechin-3-gallate (EGCg) to the subject in need thereof in an amount effective to:
  decrease the myostatin level thereby decreasing muscle function decline, improving muscle function, or both in the subject;
  wherein the EGCg is administered as part of a nutritional composition comprising at least one source of protein, at least one source of carbohydrate, and at least one source of fat; and
  wherein the source of protein is selected from the group consisting of whey protein concentrates, whey protein isolates. whey protein hydrolysates, acid caseins, sodium caseinates, calcium caseinates, potassium caseinates, casein hydrolysates, milk protein concentrates, milk protein isolates, milk protein hydrolysates, nonfat dry milk, condensed skim milk, soy protein concentrates, soy protein isolates, soy protein hydrolysates, pea protein concentrates, pea protein isolates, pea protein hydrolysates, collagen proteins, collagen protein isolates, insect proteins. and combinations thereof.

2. The method of claim 1, wherein the EGCg is administered orally.

3. The method of claim 1, wherein the EGCg is provided at eas in part by a green tea extract that contains 20-100 wt. % EGCg.

4. The method of claim 1, wherein the nutritional composition contains 50-500 kcal per serving and is in the form of a liquid or a bar.

5. The method of claim 1, wherein the EGCg is administered as a liquid nutritional product having a serving size ranging from 30 mL to 500 mL.

6. The method of claim 1, wherein the EGCg is administered once or twice daily.

7. The method of claim 1, wherein the nutritional composition further comprises a branched-chain amino acid selected from the group consisting of leucine, isoleucine, valine, and combinations thereof.

8. The method of claim 1, wherein the nutritional composition further comprises β-hydroxy-β-methylbutyrate, β-alanine, or both.

9. The method of claim 1, wherein the nutritional composition further comprises 1 gram to 3 grams of β-hydroxy-β-methylbutyrate, 15 grams to 25grams of protein, and 100 IU to 750 IU of Vitamin D.

10. The method of claim 1, wherein the method further comprises administering one or more flavan-3-ol selected from the group consisting of catechin, gallocatechin, epicatechin, epicatechin gallate, and epigallocatechin.

11. The method of claim 1, wherein the nutritional composition is a clear liquid nutritional product having a pH ranging from 2 to 5 and including 0.5wt % fat or less.

12. The method of claim 1, wherein a total of 0.1 g/day to 3g/day of EGCg is administered to the subject.

13. The method of claim 1, wherein the subject is a human.

14. The method of claim 1, wherein the subject is an elderly human.

15. The method of claim 1, wherein the subject is hospitalized or immobilized.

16. The method of claim 1, the nutritional composition comprising at least one source of protein in an amount sufficient to provide 6 grams to 50 grams of protein per serving, and 0.1 grams to 3 grams of epigallocatechin-3-gallate (EGCg) per serving.

17. A method of decreasing a myostatin level in a subject in need thereof, the method comprising administering epigallocatechin-3-gallate (EGCg) to the subject in need thereof in an amount effective to:
  decrease the myostatin level thereby decreasing muscle function decline, improving muscle function, or both in the subject;
  wherein the EGCg is administered as part of a nutritional composition; and
  wherein the nutritional composition further comprises a branched-chain amino acid selected from the group consisting of leucine, isoleucine, valine, and combinations thereof.

18. A method of decreasing a myostatin level in a subject in need thereof, the method comprising administering epigallocatechin-3-gallate (EGCg) to the subject in need thereof in an amount effective to:
  decrease the myostatin level thereby decreasing muscle function decline, improving muscle function, or both in the subject;
  wherein the EGCg is administered as part of a nutritional composition; and
  wherein the nutritional composition further comprises β-hydroxy-β-methylbutyrate, β-alanine, or both.

19. A method of decreasing a myostatin level in a subject in need thereof, the method comprising administering epigallocatechin-3-gallate (EGCg) to the subject in need thereof in an amount effective to:
  decrease the myostatin level thereby decreasing muscle function decline, improving muscle function, or both in the subject;
  wherein the EGCg is administered as part of a nutritional composition; and
  wherein the nutritional composition is a clear liquid nutritional product having a pH ranging from 2 to 5 and including 0.5 wt % fat or less.

* * * * *

UNITED STATES PATENT AND TRADEMARK OFFICE
CERTIFICATE OF CORRECTION

PATENT NO. : 9,844,531 B2
APPLICATION NO. : 14/776972
DATED : December 19, 2017
INVENTOR(S) : Sean Garvey et al.

It is certified that error appears in the above-identified patent and that said Letters Patent is hereby corrected as shown below:

Claim 3, Column 29, Line 25, Change "eas" to --least--.

Signed and Sealed this
Sixth Day of March, 2018

Andrei Iancu
*Director of the United States Patent and Trademark Office*